(12) United States Patent
Mata et al.

(10) Patent No.: US 12,256,926 B2
(45) Date of Patent: Mar. 25, 2025

(54) DEVICE FOR USE IN LAPAROSCOPIC SURGERY AND METHOD OF USE

(71) Applicant: BOLDER SURGICAL, LLC, Marlborough, MA (US)

(72) Inventors: Vincent Mata, Monroe, CT (US); Alan Bachman, Milford, CT (US); Richard N. Granger, Niwot, CO (US); Gerald Wheeler, Rochester, MA (US); Allison B. Lyle, Boulder, CO (US)

(73) Assignee: Bolder Surgical, LLC, Marlborough, MA (US)

(*) Notice: Subject to any disclaimer, the term of this patent is extended or adjusted under 35 U.S.C. 154(b) by 0 days.

(21) Appl. No.: 18/668,823

(22) Filed: May 20, 2024

(65) Prior Publication Data
US 2024/0390000 A1 Nov. 28, 2024

Related U.S. Application Data

(63) Continuation of application No. 18/051,646, filed on Nov. 1, 2022, now Pat. No. 12,082,807, which is a
(Continued)

(51) Int. Cl.
A61B 17/068 (2006.01)
A61B 17/072 (2006.01)
(Continued)

(52) U.S. Cl.
CPC ...... A61B 17/068 (2013.01); A61B 17/07207 (2013.01); A61B 2017/00991 (2013.01);
(Continued)

(58) Field of Classification Search
CPC ............ A61B 17/068; A61B 17/07207; A61B 2017/00991; A61B 2017/2901; A61B 2017/2902; A61B 2017/320052
See application file for complete search history.

(56) References Cited

U.S. PATENT DOCUMENTS 3,079,606 A 3/1963 Green
3,490,675 A 1/1970 Green
(Continued)

FOREIGN PATENT DOCUMENTS

EP 1604607 12/2005
JP 2002-165801 6/2002
(Continued)

OTHER PUBLICATIONS

Miyashita, Koji, "Notice of Reasons for Rejection" issued Dec. 22, 2020 in Japanese Patent Application No. 2019-175923 and its English translation, 9 pages.
(Continued)

Primary Examiner — Michelle Lopez
(74) Attorney, Agent, or Firm — Vista IP Law Group, LLP

(57) ABSTRACT

A device for use in laparoscopic surgery is provided. The device has a plurality of telescoping sections positioned in and movable relative to a protective sheath between an extended configuration, wherein a body section of a first one of the telescoping sections is spaced apart from a body section of a second one of the telescoping sections, and a retracted configuration wherein the body section of the first one of the telescoping sections is in contact with the body section of the second one of the telescoping sections. A tissue interaction portion is configured to interact with tissue in response to the manipulation of a device actuator.

20 Claims, 25 Drawing Sheets

Related U.S. Application Data continuation of application No. 16/985,486, filed on Aug. 5, 2020, now abandoned, which is a continuation of application No. 15/666,760, filed on Aug. 2, 2017, now Pat. No. 10,806,446, which is a continuation of application No. 14/275,753, filed on May 12, 2014, now Pat. No. 9,750,497.

(51) Int. Cl.
  *A61B 17/00* (2006.01)
  *A61B 17/29* (2006.01)
  *A61B 17/32* (2006.01)

(52) U.S. Cl.
  CPC ............... *A61B 2017/2901* (2013.01); *A61B 2017/2902* (2013.01); *A61B 2017/320052* (2013.01)

(56) References Cited

U.S. PATENT DOCUMENTS

| | | | |
|---|---|---|---|
| 3,499,571 | A | 3/1970 | Green et al. |
| 3,499,591 | A | 3/1970 | Green |
| 4,438,766 | A | 3/1984 | Bowers |
| 5,040,715 | A | 8/1991 | Green |
| 5,240,163 | A | 8/1993 | Stein et al. |
| 5,307,976 | A | 5/1994 | Green |
| 5,312,023 | A | 5/1994 | Green |
| 5,318,221 | A | 6/1994 | Green |
| 5,326,013 | A | 7/1994 | Green |
| 5,332,142 | A | 7/1994 | Robinson |
| 5,462,546 | A | 10/1995 | Rydell |
| 5,673,841 | A | 10/1997 | Schulze |
| 5,865,361 | A | 2/1999 | Milliman |
| 6,763,993 | B2 | 7/2004 | Bolduc et al. |
| RE38,708 | E | 3/2005 | Bolanos |
| 7,637,409 | B2 | 12/2009 | Marczyk |
| 7,841,502 | B2 | 11/2010 | Walberg |
| 7,950,560 | B2 | 5/2011 | Zemlok et al. |
| 8,006,886 | B2 | 8/2011 | Sonnenschein |
| 8,517,240 | B1 | 8/2013 | Mata |
| 9,539,021 | B2 | 1/2017 | Mata et al. |
| 9,750,497 | B2 | 9/2017 | Mata et al. |
| 10,806,446 | B2 | 10/2020 | Mata |
| 2004/0232201 | A1 | 11/2004 | Wenchell et al. |
| 2005/0023324 | A1 | 2/2005 | Doll et al. |
| 2005/0222616 | A1 | 10/2005 | Rehty et al. |
| 2010/0193567 | A1 | 8/2010 | Scheib |
| 2011/0290851 | A1 | 12/2011 | Shelton, IV |
| 2012/0080332 | A1 | 4/2012 | Shelton, IV |
| 2012/0232339 | A1 | 9/2012 | Csiky |
| 2013/0008937 | A1 | 1/2013 | Viola |
| 2017/0007236 | A1 | 1/2017 | Shelton, IV et al. |
| 2017/0231633 | A1 | 8/2017 | Marczyk et al. |
| 2018/0125485 | A1 | 5/2018 | Beardsley et al. |
| 2018/0250006 | A1 | 9/2018 | Bucciaglia et al. |
| 2020/0360016 | A1 | 11/2020 | Mata |

FOREIGN PATENT DOCUMENTS

| | | |
|---|---|---|
| JP | 2010-069304 | 4/2010 |
| WO | WO 2010/027693 | 11/2010 |
| WO | WO 2011/027183 | 3/2011 |
| WO | WO 2012/0040981 | 4/2012 |
| WO | WO 2014/107393 | 7/2014 |

OTHER PUBLICATIONS

Aoki, Atsushi "Amendment and Response" filed with the Japanese Patent Office on Jun. 7, 2021 and an English translation of the amended claims, in Japanese Patent Application No. 2019-175923, 7 pages.

Miyashita, Koji, "Notice of Allowance," mailed Jun. 22, 2021, in Japanese Patent Application No. 2019-175923, No English translation available, 3 pages.

Assion, Jean-Charles, Extended European Search Report for European Application No. 13870240.2, Jan. 19, 2017, 18 pages, European Patent Office, Munich Germany.

Assion, Jean Charles, Supplementary Partial European Search Report, re European Application No. 13870240.2, Aug. 16, 2016, 11 pages, EPO, Munich, Germany.

Inone, Tetsuo, Office Action (translation thereof) re Japanese Patent Application No. 2015-551727, Nov. 1, 2016, 3 pages, JPO, Japan.

Krynski, William, "International Search Report and Written Opinion re Application No. PCT/US2013/77801", Mar. 3, 2014, 8 pages, USPTO, Alexandria, Virginia.

Lopez, Michelle, Office Action re U.S. Appl. No. 13/952,630, Apr. 18, 2016, 24 pages, USPTO, Alexandria, Virgina.

Schneider, Laura, Response to Office Action re U.S. Appl. No. 13/952,630, Jul. 8, 2016, 9 pages, USPTO, Alexandria, Virgina.

Lopez, Michelle, Office Action re U.S. Appl. No. 14/275,753, Nov. 9, 2016, 18 pages, USPTO, Alexandira, Virginia.

Moon, Kihwan, International Preliminary Report on Patentability re PCT Application No. PCT/US2013/077801, Jul. 7, 2015, 5 pages, WIPO, Geneva, Switzerland.

Yamaguchi, Kenichi, Office Action re Japanese Patent Application No. 2017-173942, (translation thereof), May 7, 2019, 6 pages, JPO, Japan.

Oya, Shizuo, Office Action re Japanese Patent Application No. 2017-173942, (translation thereof), Aug. 14, 2018, 5 pages, JPO, Japan.

Scheider, Laura, Response to Office Action re U.S. Appl. No. 14/275,753, Feb. 1, 2017, 11 pages, USPTO, Alexandria, Virginia.

Moon, Kihwan, International Preliminary Report on Patentability re PCT Application No. PCT/US2013/077801, Jul. 16, 2015, 5 pages, Published in WO.

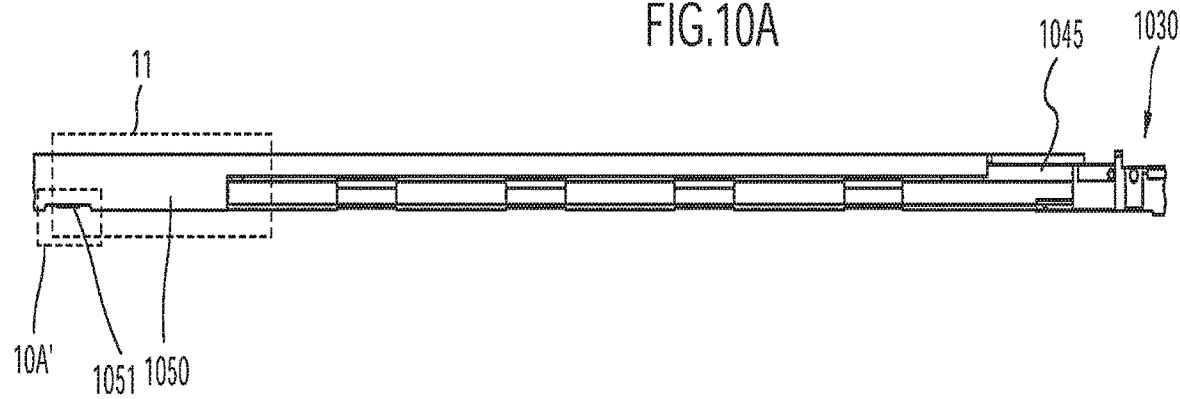
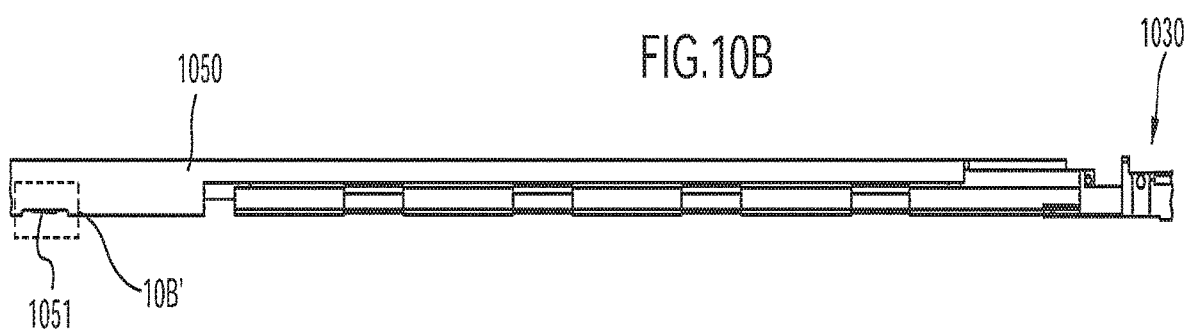
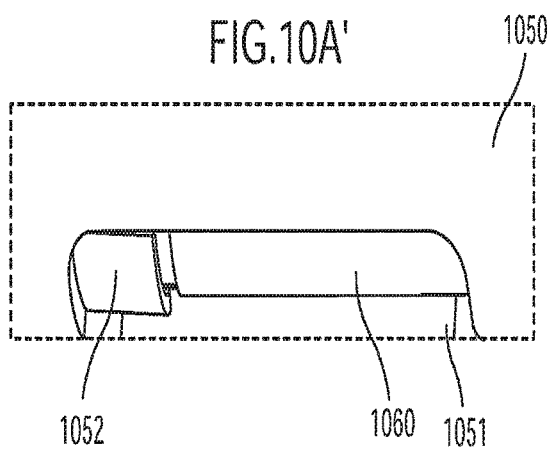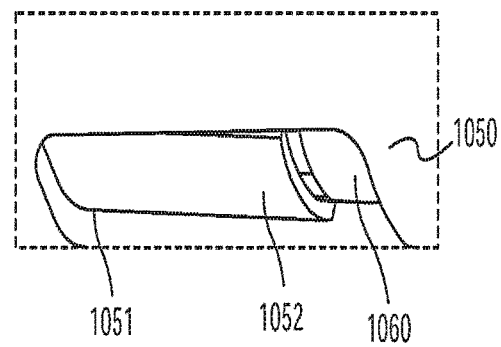

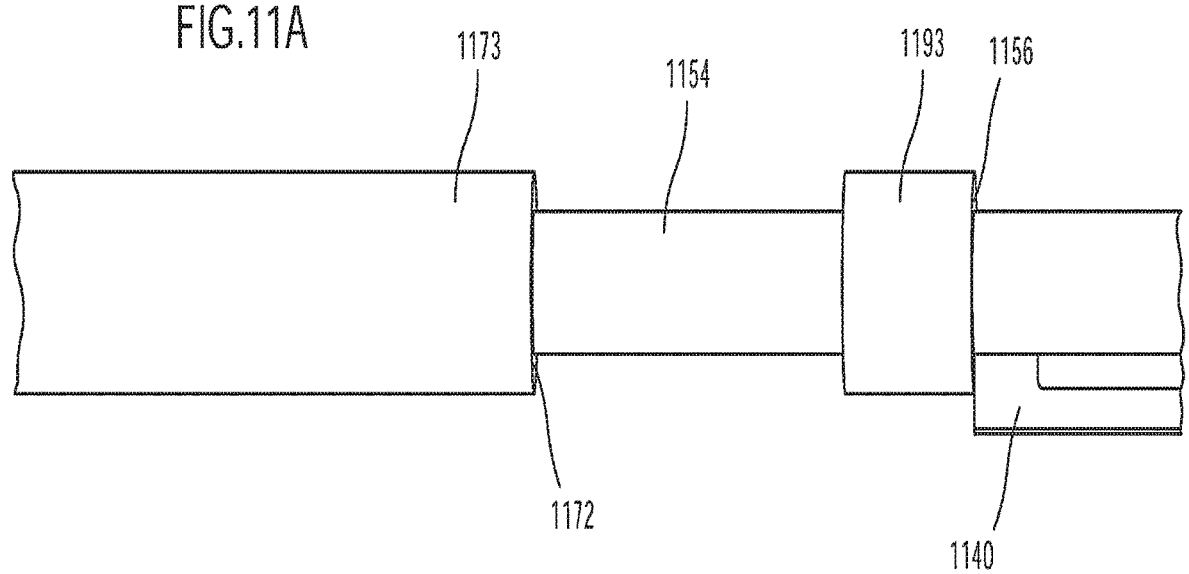
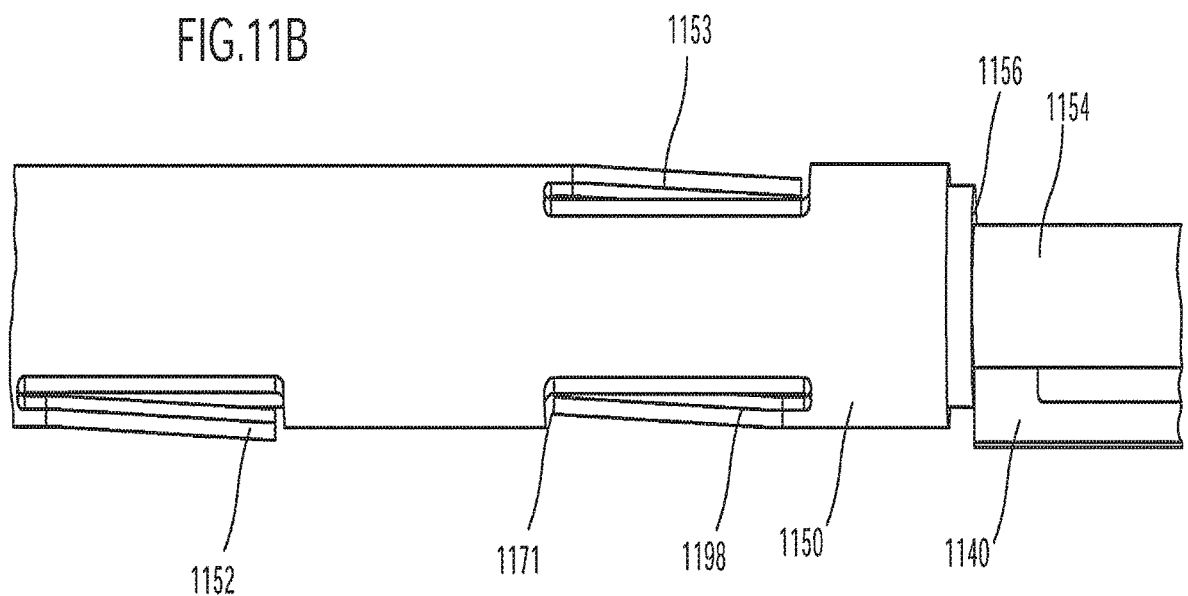

DEVICE FOR USE IN LAPAROSCOPIC SURGERY AND METHOD OF USE

CROSS-REFERENCE TO RELATED APPLICATIONS

This application is a continuation of U.S. patent application Ser. No. 18/051,646, filed Nov. 1, 2022 and entitled "Device for Use in Laparoscopic Surgery and Method of Use," which is a continuation of U.S. patent application Ser. No. 16/985,486, filed Aug. 5, 2020 and entitled "Device for Use in Laparoscopic Surgery and Method of Use," which is a continuation of U.S. patent application Ser. No. 15/666,760, filed Aug. 2, 2017 and entitled "Device for Use in Laparoscopic Surgery and Method of Use," now U.S. Pat. No. 10,806,466, which is a continuation of U.S. patent application Ser. No. 14/275,753, filed May 12, 2014 and entitled "Device for Use in Laparoscopic Surgery and Method of Use," now U.S. Pat. No. 9,750,497, the disclosures of which are incorporated herein by reference in their entireties.

FIELD OF THE INVENTION

This invention is related to medical devices. Specifically, but not intended to limit the invention, embodiments of the invention are related to a medical device adapted to extend and provide gripping, cutting, and stapling features.

BACKGROUND OF THE INVENTION

Surgical staplers may not be designed for use on particularly small tissue sections or organs, such as, for example, those seen in pediatric surgery. For example, a stapling mechanism and any associated gripping and cutting devices may be inappropriately sized and/or may operate ineffectively or inefficiently during pediatric procedures, where it may be desired to have a cannula that is around 5 millimeters in diameter or less.

For example, the prior art devices are sized and developed with various support structures to provide the rigidity necessary to function. The support structures include rigid I-beams, other rigid structures, and/or separate manually-manipulated structures for controlling movement of tissue manipulation devices. However, when developing a laparoscopic surgical device for use on small tissue sections such as seen in pediatric surgery, manufacturing sizes cannot simply be scaled down without further modification.

SUMMARY OF THE INVENTION

To overcome the deficiencies described above, in one example, a device for use in laparoscopic surgery is provided.

An exemplary device is described below.

An exemplary device for use in laparoscopic surgery has a distal end having a tissue interaction portion, a proximal end having a device actuator, and a protective sheath having a distal end and a proximal end and extending at least partially between the tissue interaction portion and the device actuator. A plurality of telescoping sections are positioned in and movable relative to the protective sheath between an extended configuration, wherein a body section of a first one of the telescoping sections is spaced apart from a body section of a second one of the telescoping sections, and a retracted configuration wherein the body section of the first one of the telescoping sections is in contact with the body section of the second one of the telescoping sections. The plurality of telescoping sections are movable from the extended configuration in response to a manipulation of the device actuator. The tissue interaction portion is configured to interact with tissue in response to the manipulation of the device actuator.

Illustrative embodiments of the present invention that are shown in the drawings are summarized herein. These and other embodiments are more fully described in the Detailed Description section. It is to be understood, however, that there is no intention to limit the invention to the forms described in this Summary of the Invention or in the Detailed Description. One skilled in the art can recognize that there are numerous modifications, equivalents, and alternative constructions that fall within the spirit and scope of the invention as expressed in the claims.

BRIEF DESCRIPTION ON THE DRAWINGS

Various objects and advantages and a more complete understanding of the present invention are apparent and more readily appreciated by reference to the following Detailed Description and to the appended claims when taken in conjunction with the accompanying Drawings, where like or similar elements are designated with identical reference numerals throughout the several views and wherein:

FIG. 10A illustrates a side view of an extension portion and a portion of a tissue interaction portion, with an outer sheath being removed, in a retracted location according to one embodiment of the invention;

Figure 12:
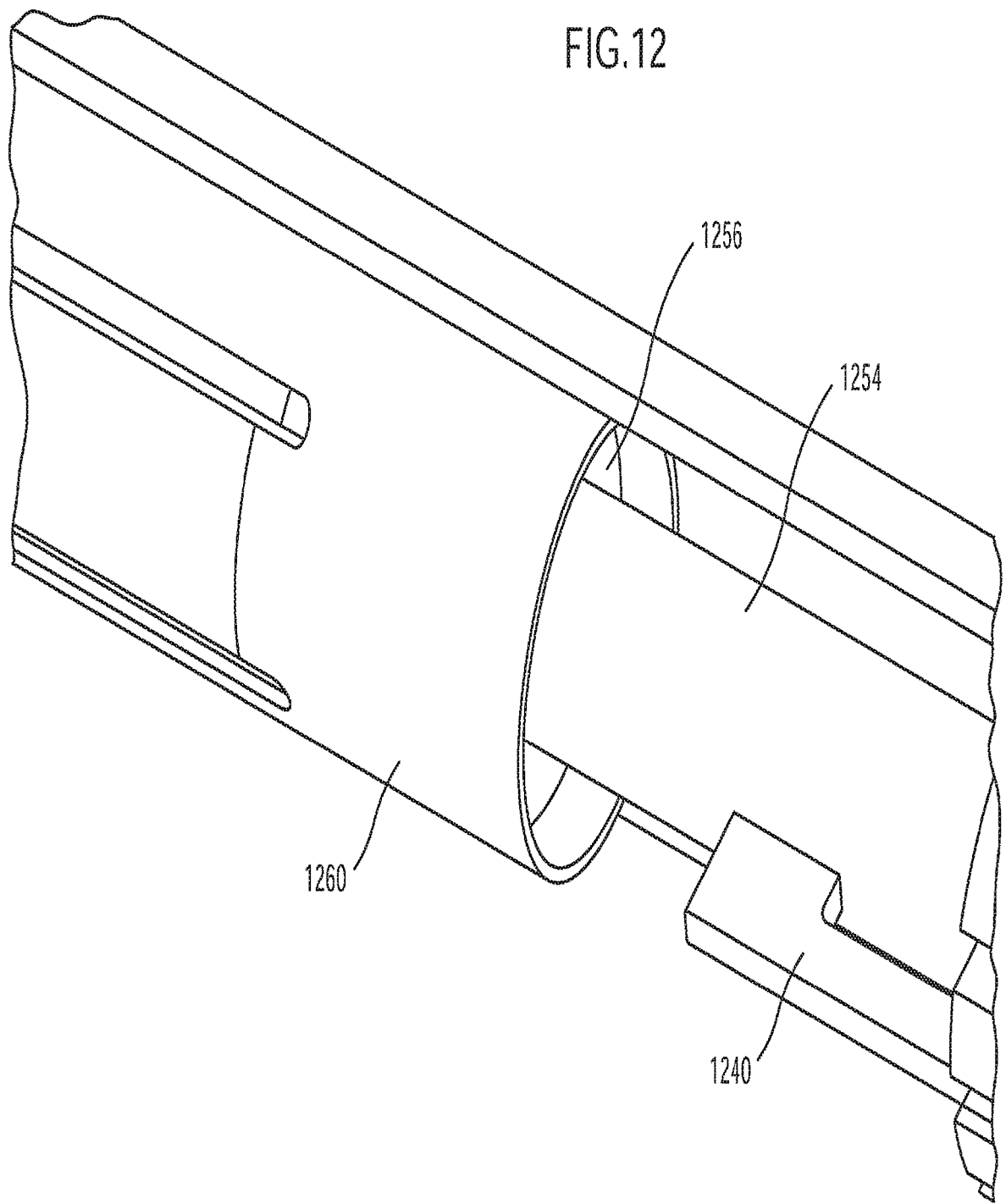
Figure 13:
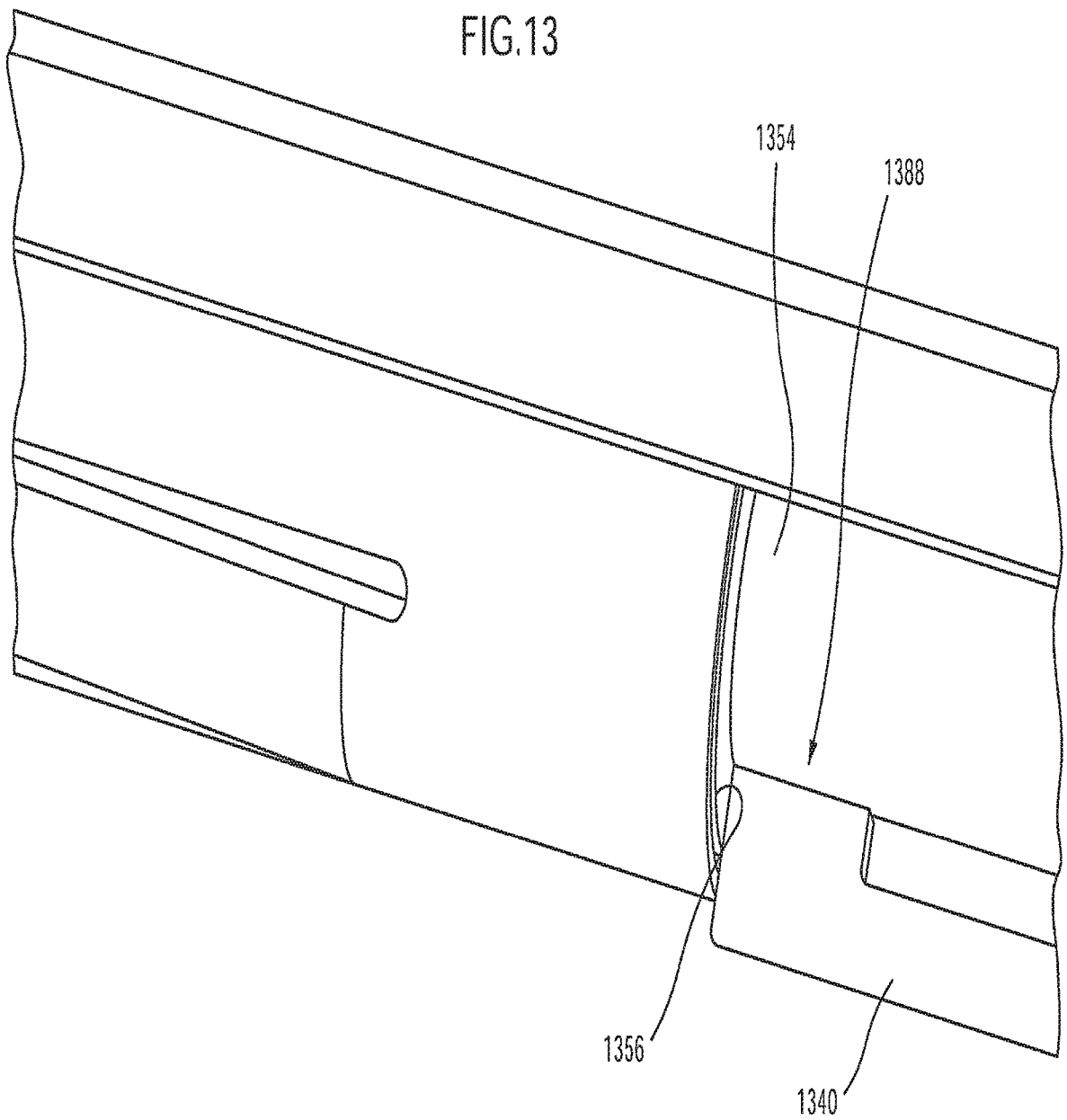
Figure 14:
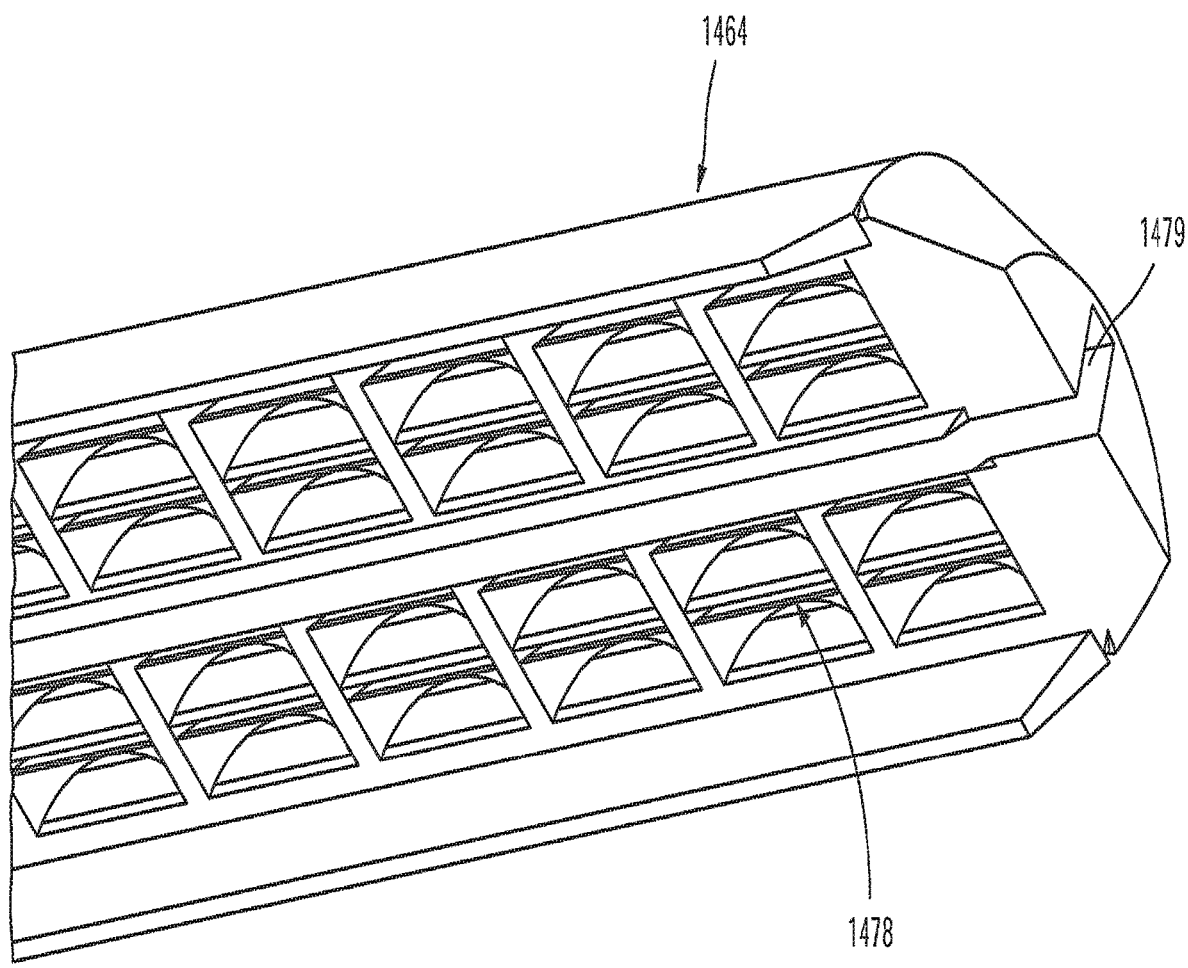
Figure 15:
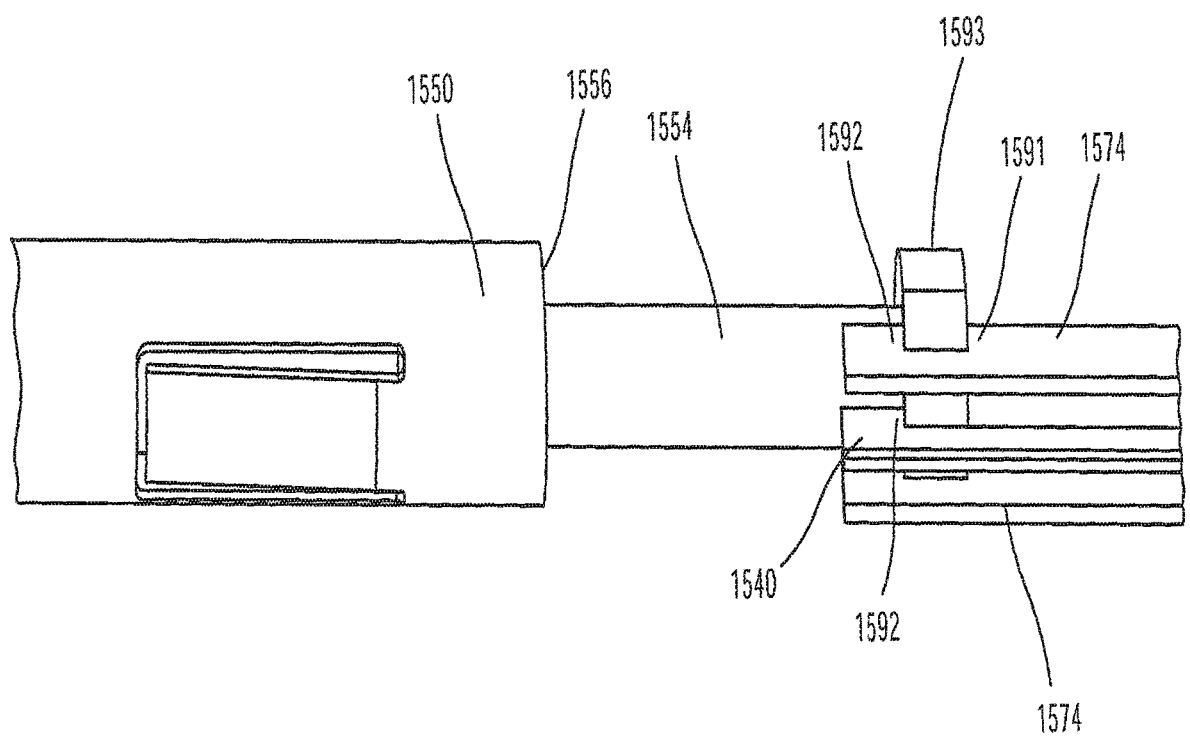
Figure 16:
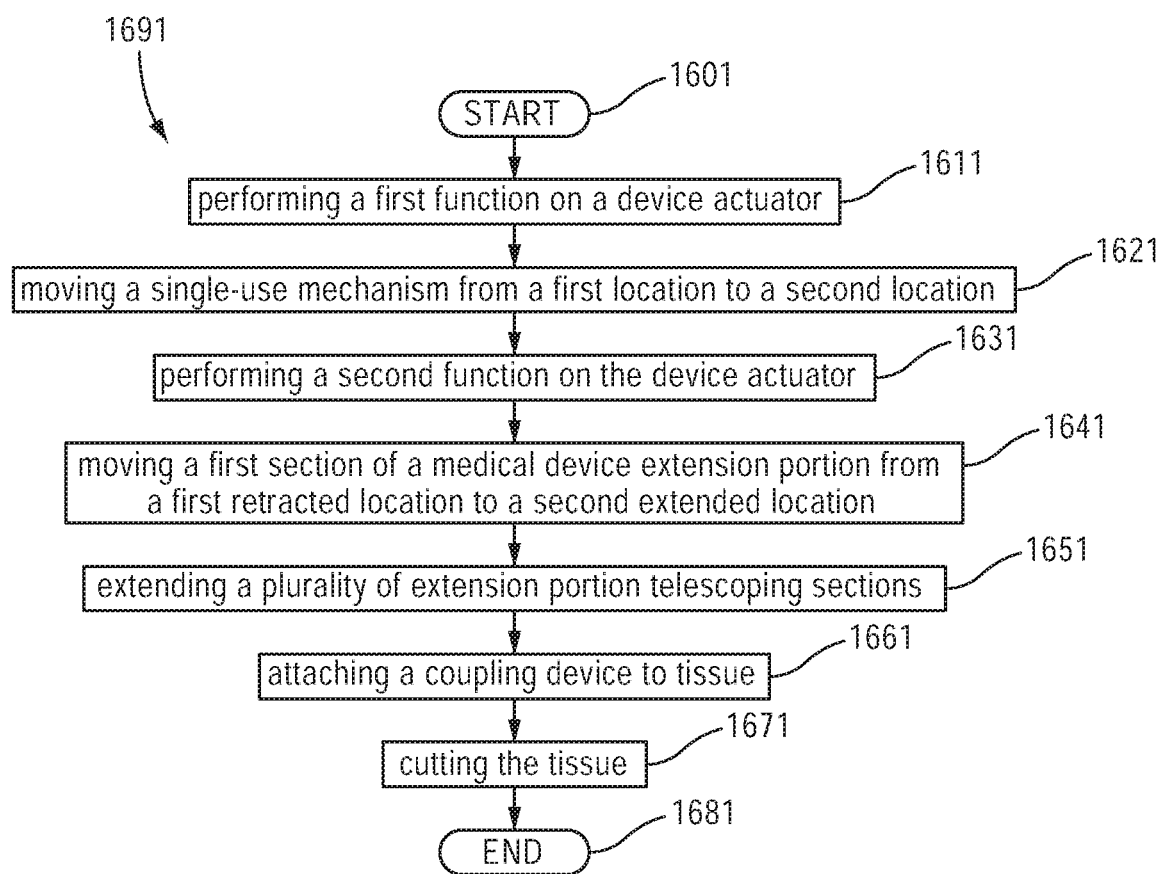
Figure 17:
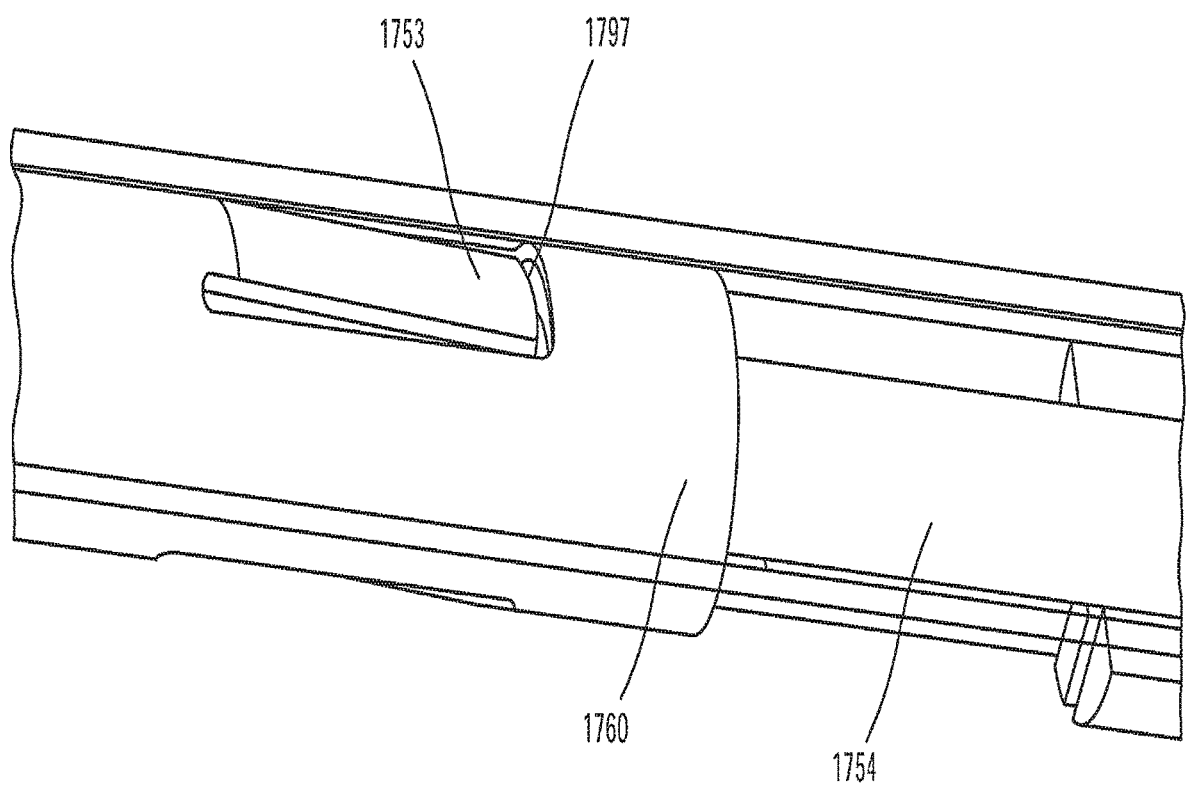
Figure 18:
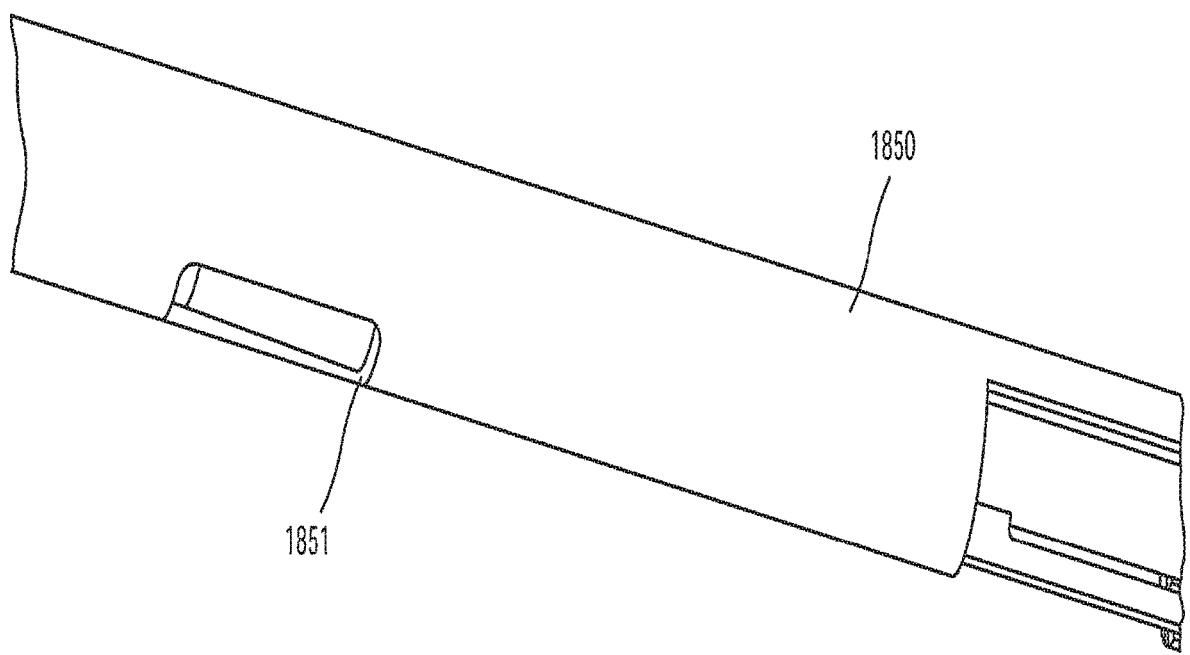

FIG. 10A' illustrates an isometric view of section 10A' in FIG. 10A according to one embodiment of the invention;

FIG. 10B illustrates a side view of an extension portion and a portion of a tissue interaction portion, with an outer sheath being removed, in an extended location according to one embodiment of the invention;

FIG. 10B' illustrates an isometric view of section 10B' in FIG. 10B according to one embodiment of the invention;

FIG. 11A illustrates a side view of section 11 in FIG. 10A with a clamping sheath and a locking sheath removed according to one embodiment of the invention;

FIG. 11B illustrates a side view of section 11 in FIG. 10A with a locking sheath removed according to one embodiment of the invention;

FIG. 12 illustrates a close-up isometric view of the locking sheath and staple rod according to one embodiment of the invention;

FIG. 13 illustrates another close-up isometric view of the locking sheath and staple rod according to one embodiment of the invention;

FIG. 14 illustrates an isometric view of a clamping section undercarriage according to one embodiment of the invention;

FIG. 15 illustrates an isometric vie w of a staple pusher, staple rods and cutting mechanism according to one embodiment of the invention;

FIG. 16 illustrates a flowchart that depicts a method that may be carried out in connection with the embodiments described herein;

FIG. 17 illustrates a close-up isometric view of a transparent locking sheath, and a clamping sheath and staple rod according to one embodiment of the invention; and FIG. 18 illustrates a locking sheath interacting with a clamping sheath according to one embodiment of the invention.

Figure 19:
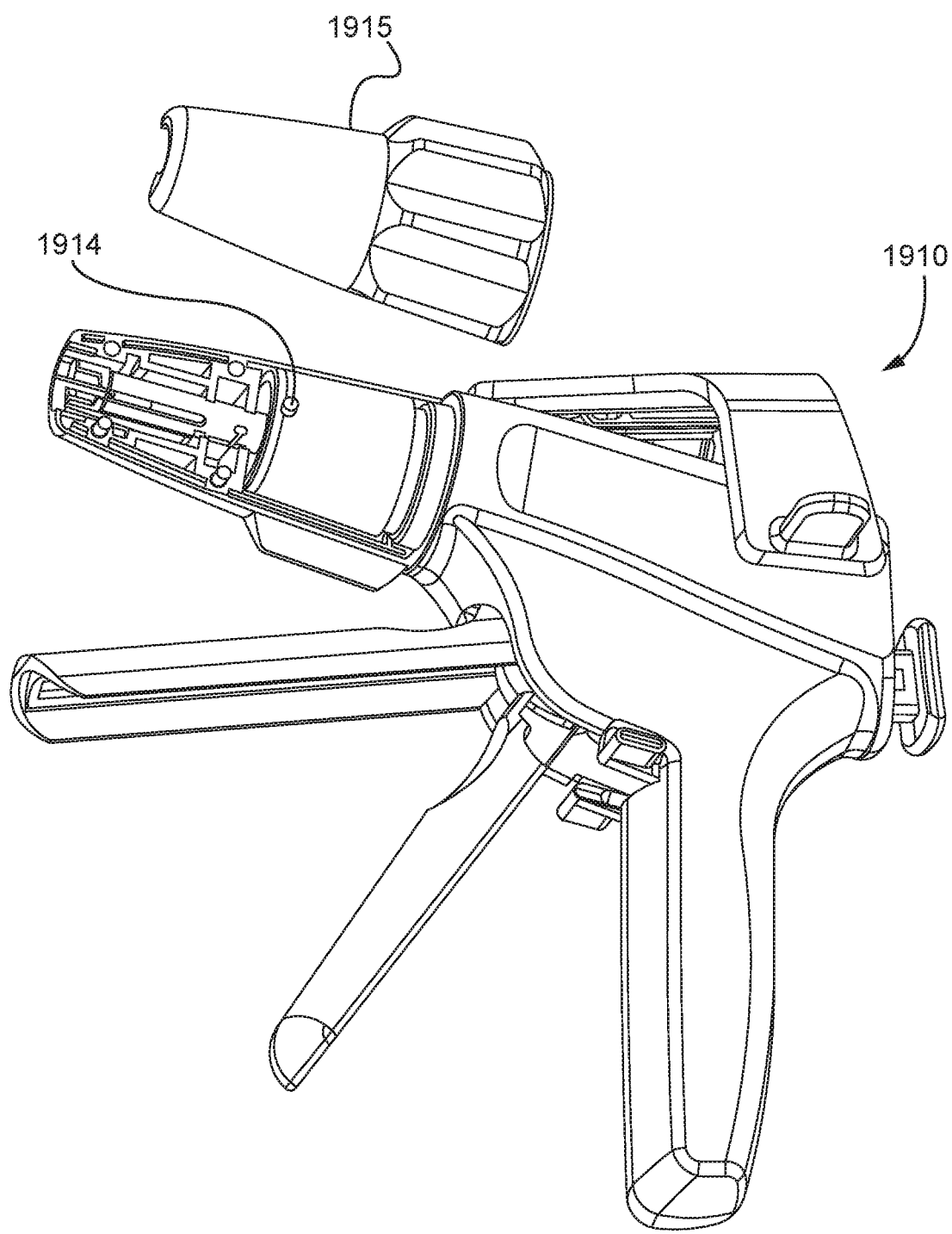

FIG. 19 illustrates an isometric exploded view of an actuator according to another embodiment of the invention.

Figure 20:
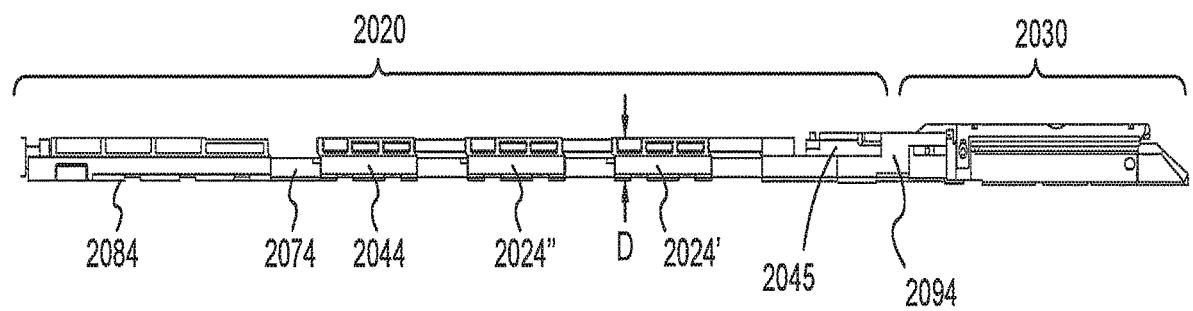

FIG. 20 illustrates a side view of a device without the outer sheath and actuator according to another embodiment of the invention.

Figure 21:
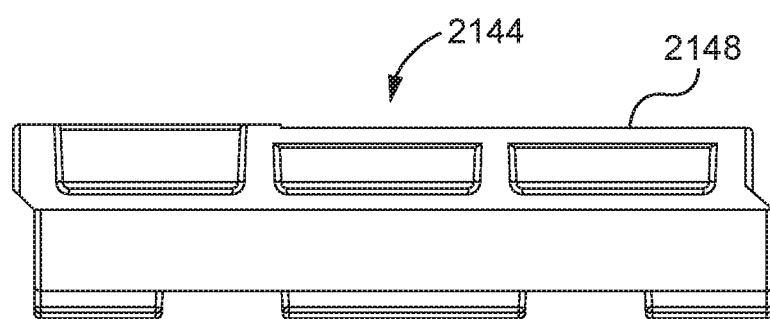

FIG. 21 illustrates a side view of the spacer section illustrated in FIG. 20.

Figure 22:
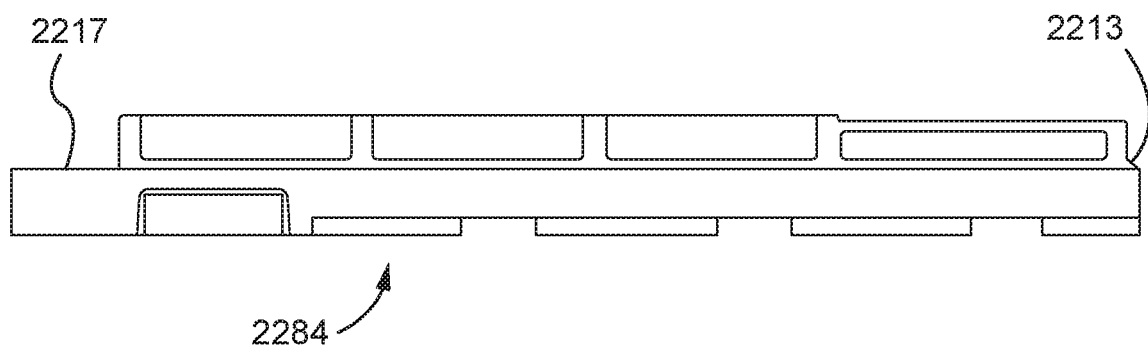

FIG. 22 illustrates a side view of the elongated spacer section illustrated in FIG. 20.

Figure 23A:
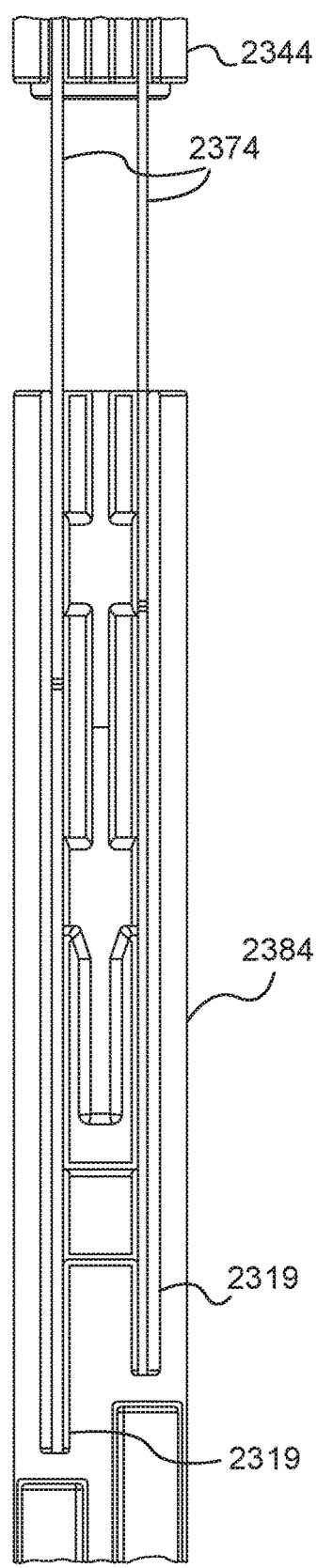

FIG. 23A illustrates a top view of a reload lockout feature in a pre-fire position, according to another embodiment of the invention.

Figure 23B:
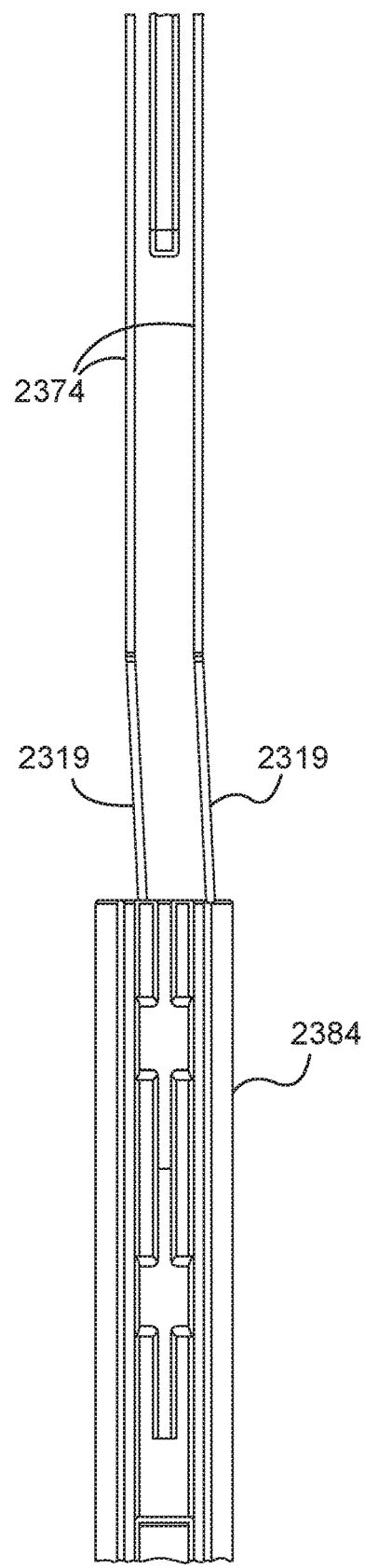

FIG. 23B illustrates a top view of a reload lockout feature in a post-fire position, according to another embodiment of the invention.

Figure 24A:
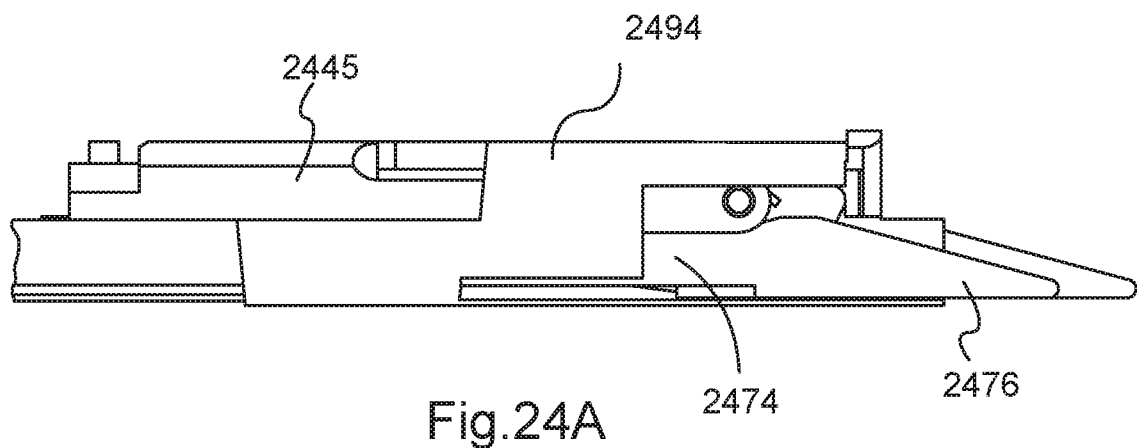

FIG. 24A illustrates a side view of a catch feature in a post-fire position, according to another embodiment of the invention.

Figure 24B:
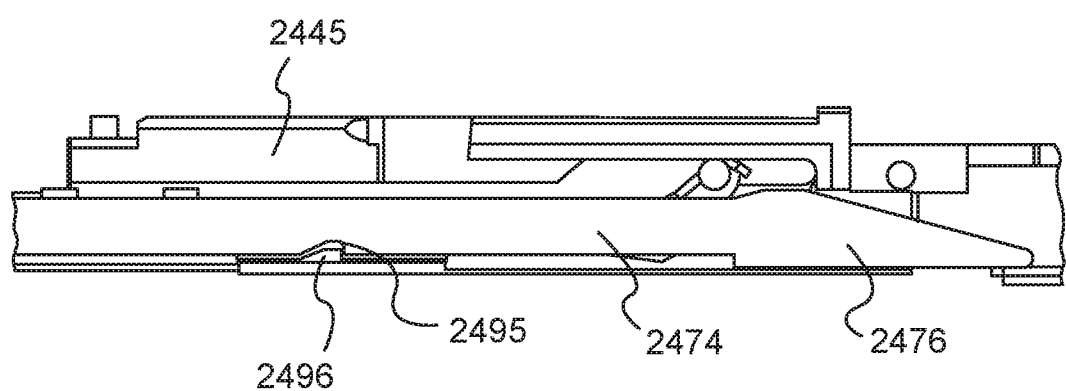

FIG. 24B illustrates a partial section view of the catch feature in FIG. 24A, according to another embodiment of the invention.

Figure 25:
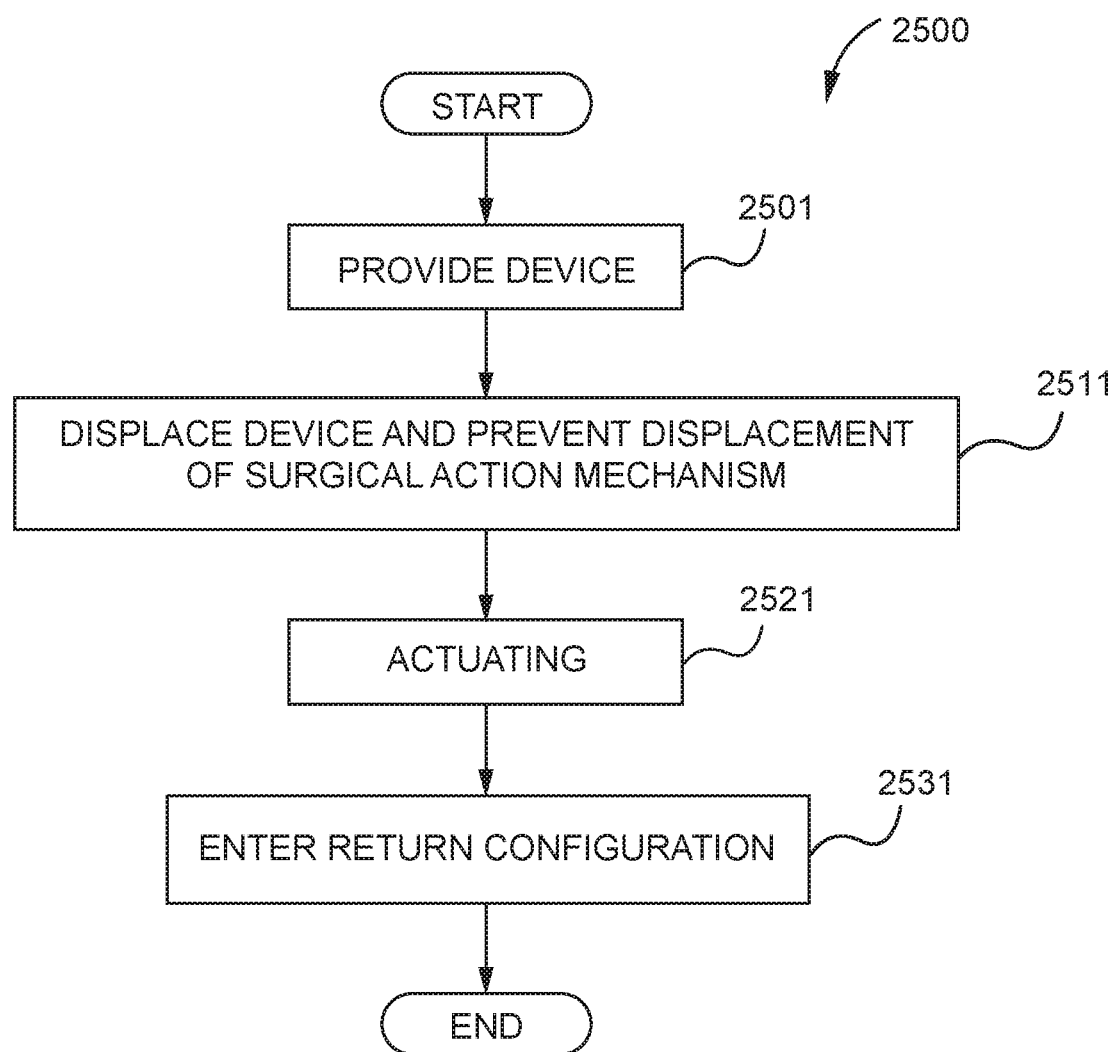

FIG. 25 illustrates a flowchart of a method according to one embodiment of the invention.

DETAILED DESCRIPTION

Figure 1:
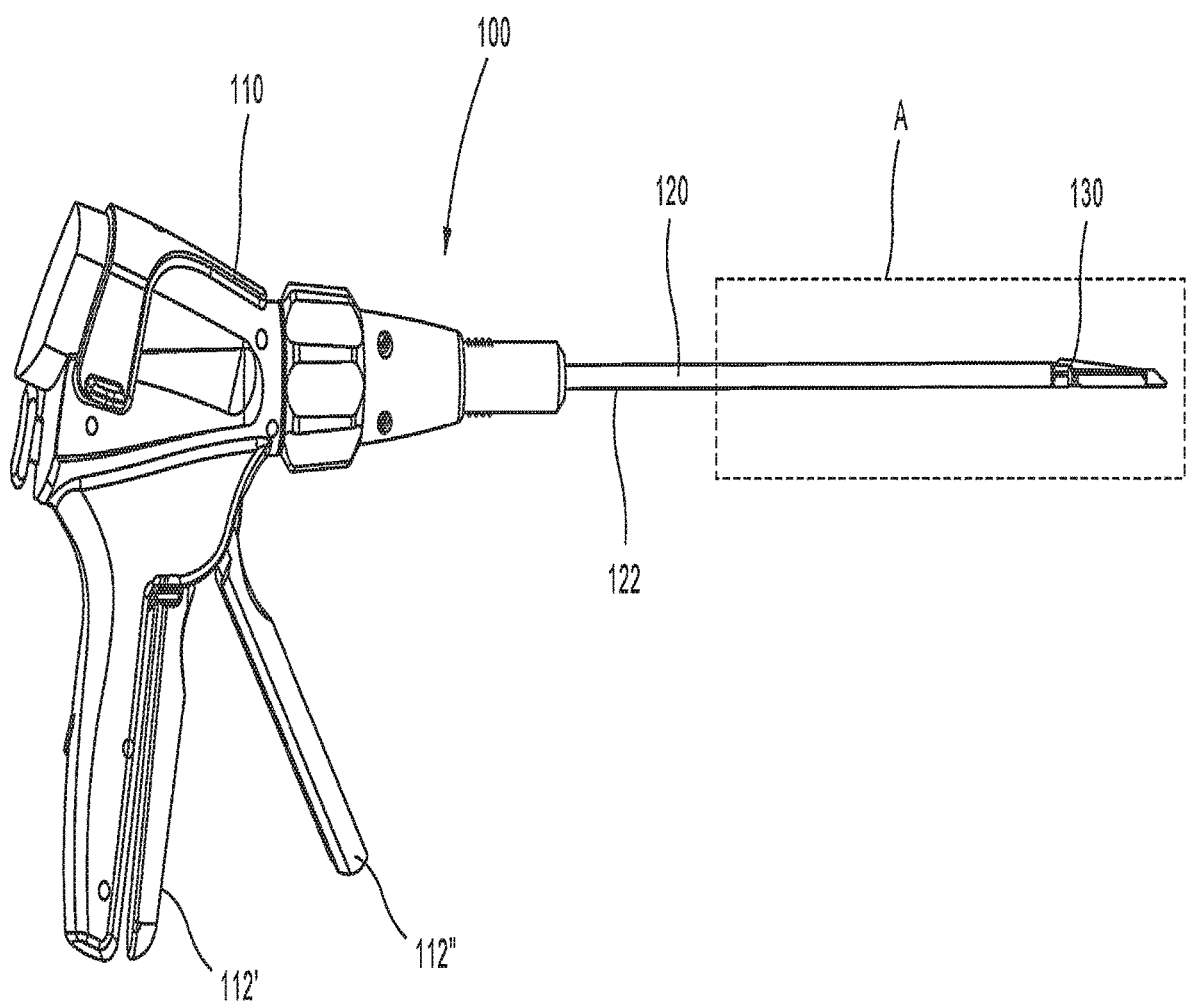
FIG. 1 illustrates a side view of a medical device according to one embodiment of the invention.

Turning first to FIG. 1, seen is an embodiment of a medical device 100. Medical device 100 comprises an actuator 110, an extension portion 120 operatively coupled to the actuator 110, and a tissue interaction portion 130 operatively coupled to the extension portion 120. The term operatively is used throughout the specification and claims to describe something that produces an effect. For example, here the extension portion 120 is operatively coupled to the actuator 110 and the tissue interaction portion 130 is operatively coupled to the extension portion 120. Therefore, and as described below, each of these coupled portions of the device 100 are adapted to produce an effect between the coupled portions.

Figure 2:
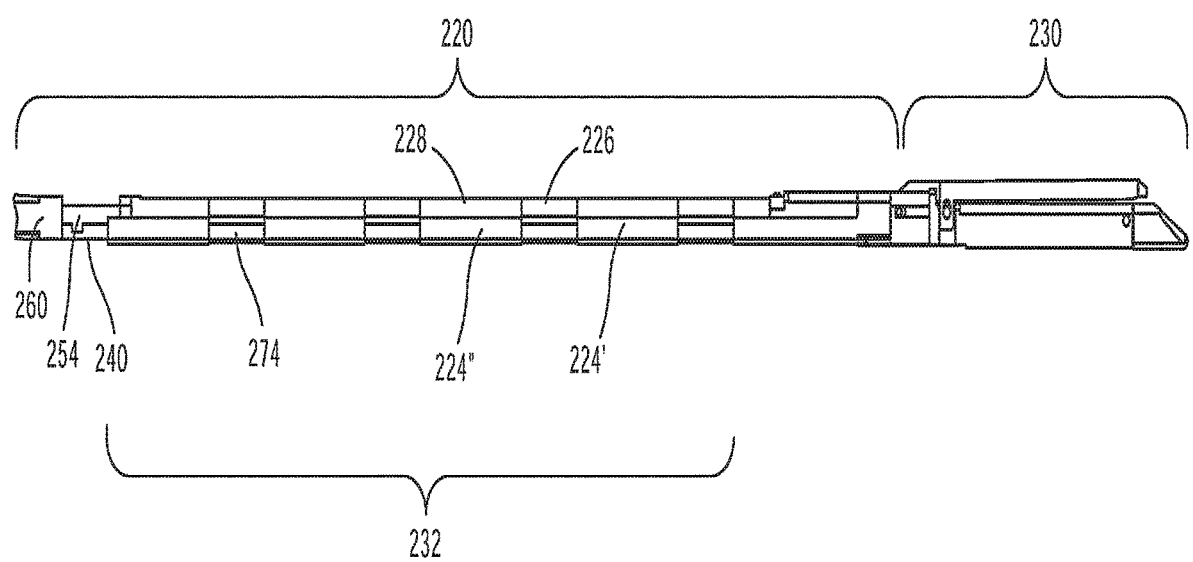
FIG. 2 illustrates a side-view of section A from FIG. 1 with an outer sheath being removed from the device according to one embodiment of the invention.

Turning to FIG. 2, seen is a close-up view of a section of the extension portion 220 and the tissue interaction portion 130, as seen in Box "A" from FIG. 1, but with the outer sheath 122 seen in FIG. 1 removed from the extension portion 120. The outer sheath 122 may comprise a protective sheath and may keep one or more of the telescoping sections 224 as seen in FIG. 2, properly aligned. A clamping sheath 1050, as described below, with references to FIG. 10A, and elsewhere, has also been removed from the extension portion 220 in FIG. 2. However, the locking sheath 260 remains. As seen, one embodiment of the extension portion 220 comprises a plurality of telescoping sections 224. At least two of the telescoping sections 224 may comprise a first and a second telescoping section. One embodiment of the medical device 220 may comprise two or more telescoping sections 224. The telescoping section 224 reference numeral, and/or any other reference numeral, may be shown with one or more prime symbols: "'".

Figure 3:
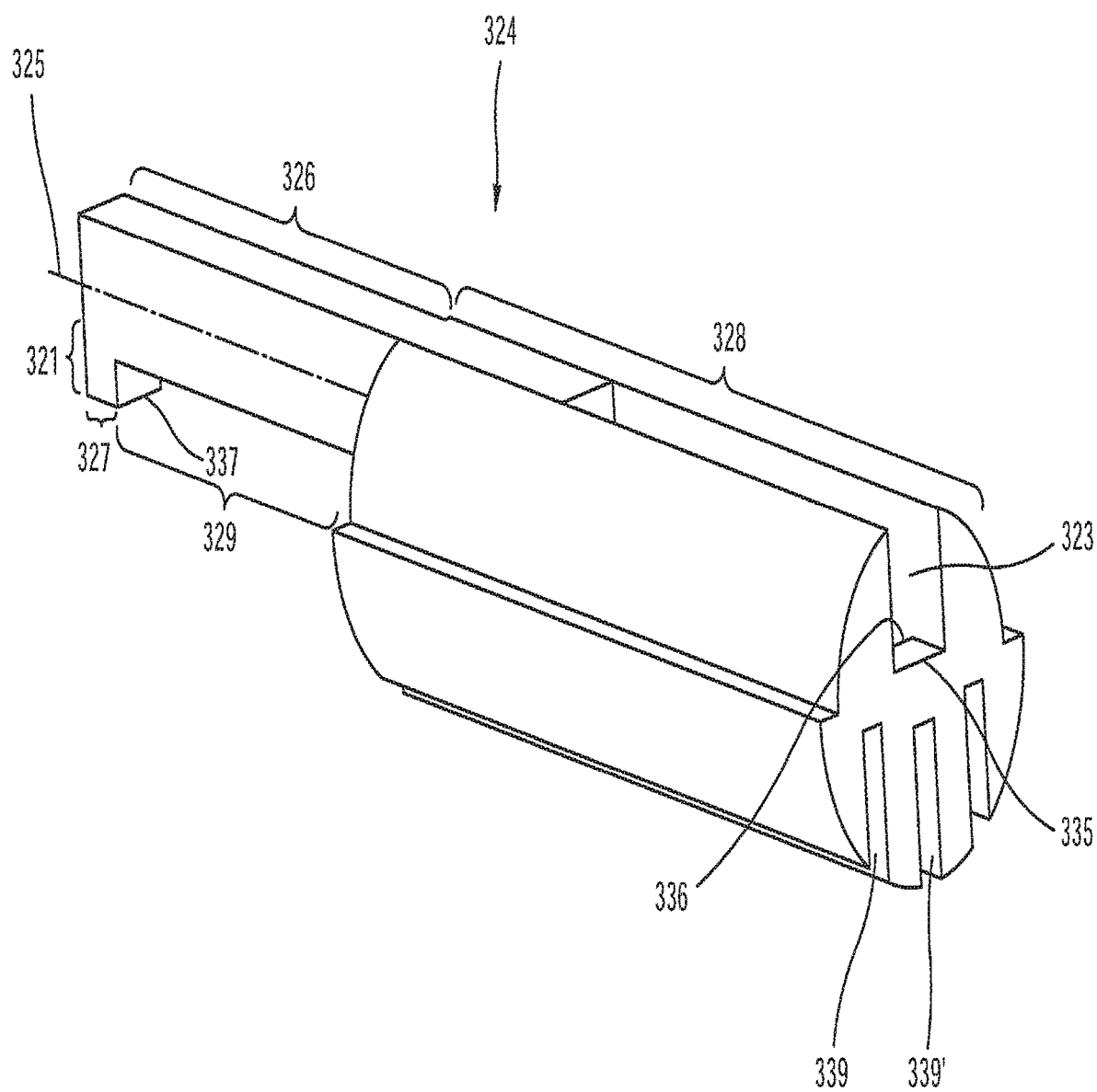
FIG. 3 illustrates an isometric view of a telescoping section device according to one embodiment of the invention.

Turning now to FIG. 3, seen is one example of a telescoping section 324. It is contemplated that other types of telescoping sections 324 may be used. The telescoping section 324 seen in FIG. 3 comprises an attachment section 326 and a body section 328. The attachment section 324 may be adapted to couple to another telescoping section 324, while the body section 328 may be adapted to receive the attachment section 324 of another telescoping section 324. The attachment section 326 may comprise at least one extended hook section that comprises a head portion 327 and a neck portion 329. The head portion 327 may comprise at least one extension section 321 extending radially outward from an attachment section longitudinal axis 325. In FIG. 3, the extension section 321 extends outward in a substantially vertical direction. However, the extension section 321 may extend in a substantially horizontal direction and/or any other direction relative to the attachment section longitudinal axis 325.

The body section 228 may either couple or integrate to one or more portions of the extended hook section. The term "couple," "coupling," or any variation thereof within the specification and claims refers to joining two separate items together. One type of coupling may involve using a coupling mechanism such as, but not limited, to, a bolting device. However, other coupling mechanisms such as latching, magnetic, or other coupling mechanisms may be used, where appropriate. Alternatively, where otherwise stated, coupling may also refer to "integrated." The term "integrated" or any variation thereof within the specification and claims refers to combining two or more parts to create a whole and single, indivisible part, where appropriate.

Figure 4:
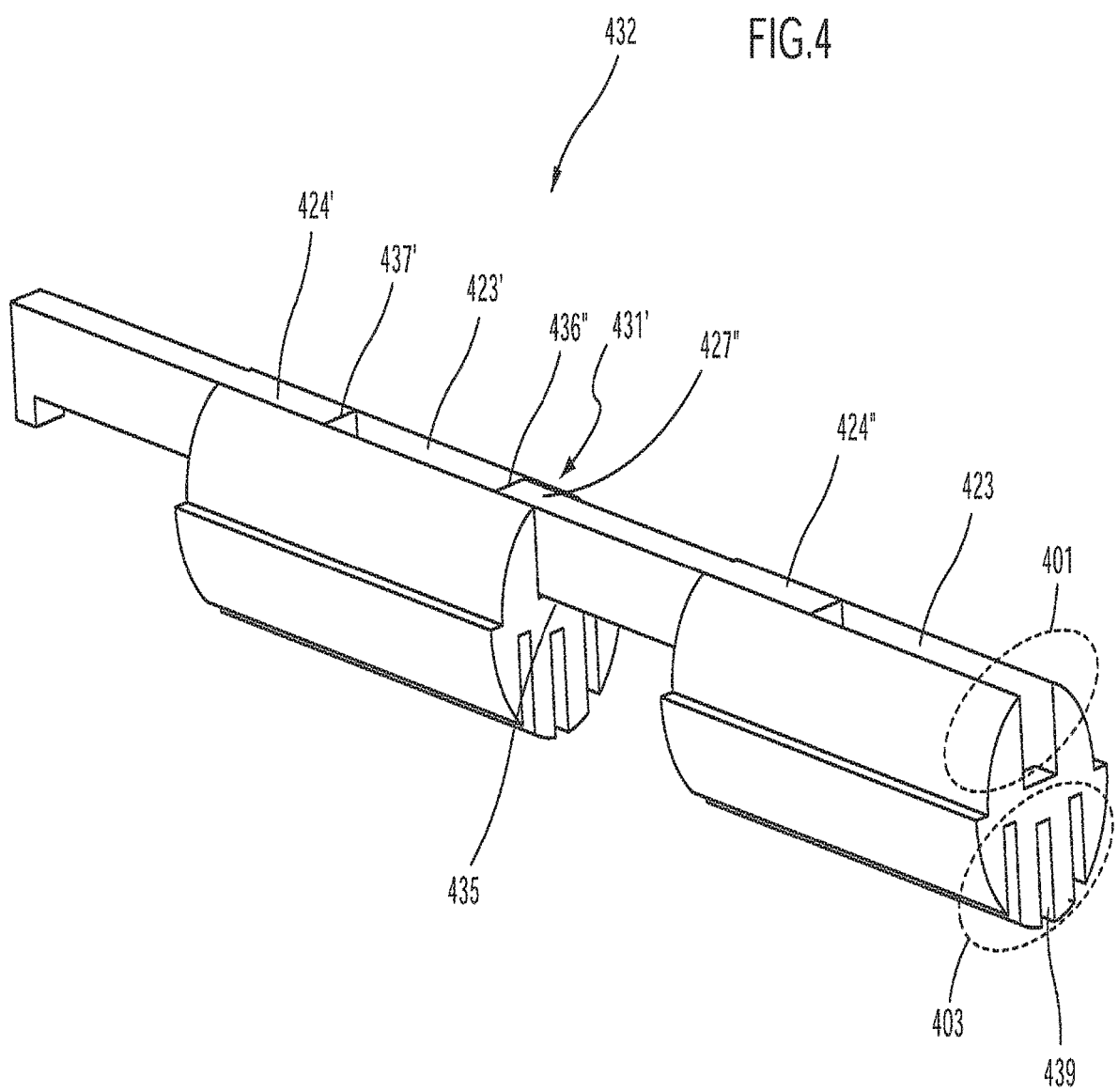
FIG. 4 illustrates an isometric view of operatively coupled and extended first and second telescoping sections according to one embodiment of the invention.

In one embodiment, the body section 328 may comprise at least one body section notch 323 adapted to slidably receive at least a portion of the attachment section 326. For example, and as seen in FIG. 4, a proximal end 431' of the body section notch 423' of a first telescoping section 424' may receive the head portion 427" of a second telescoping section 424" when the telescoping sections 424 are in an extended setting 432 as seen in FIG. 4. The extended setting 432 and retracted setting 534 seen in FIG. 5 may also be referred to as an extension section extended setting 432 and retracted setting 534. Returning now to FIG. 3, seen is a notch lip 335. The notch lip 335 may comprise a forward edge 336 which may interact with a trailing edge 337 of the head portion 327. Returning to FIG. 4, the interaction between the notch lip 435 of the first telescoping section 424' may prevent the head portion 427" of the second telescoping section 424" from sliding out of the notch 423' and may therefore keep the first and second telescoping sections coupled.

Figure 5:
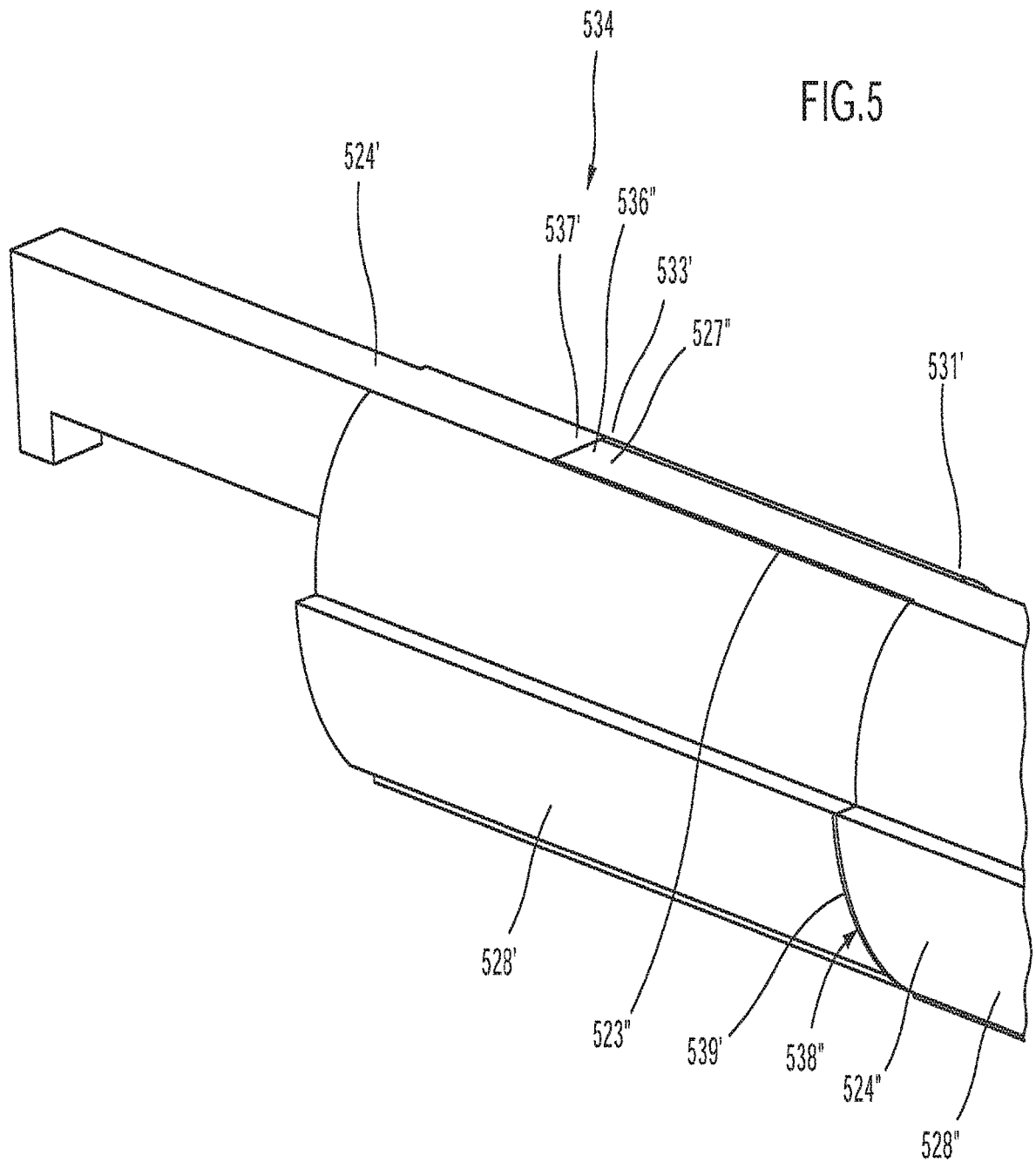
FIG. 5 illustrates an isometric view of operatively coupled and retracted first and second telescoping sections according to one embodiment of the invention.

Turning now to FIG. 5, seen are a first telescoping section 524' and a second telescoping section 524" in a retracted setting 534. In moving from the extended setting 432 seen in FIG. 4 to the retracted setting 524 in FIG. 5, or vice versa, the head portion 527" of the second telescoping section 524" may slide along the notch 523' between the proximal end 531' and the distal end 533' of the notch 523'. In the retracted setting 534, a leading edge 536" of the head 527" may interact with a rear notch edge 537'. The leading edge 436" and rear notch edge 437' are also seen in FIG. 4. Similarly, a leading edge 538" of a body section 528" of the second telescoping section 524" may interact with a trailing edge 539' of the body section 528' of the first telescoping section 524'. The term interact may refer to "contacting" with the contacting substantially preventing further movement of one or more of the telescoping sections 524', 524" in a specific direction such as, but not limited to, preventing additional movement of the second telescoping section 524" in a direction the second telescoping section 524" is moving prior to interacting with the edge 537' and lip 435, respectively. As such, in returning to FIG. 2, shown is an attachment section 226 of at least one first telescoping section 224' operatively coupled to the body section 338 of at least one second telescoping section 224" in an extended setting 232.

Figure 6A:
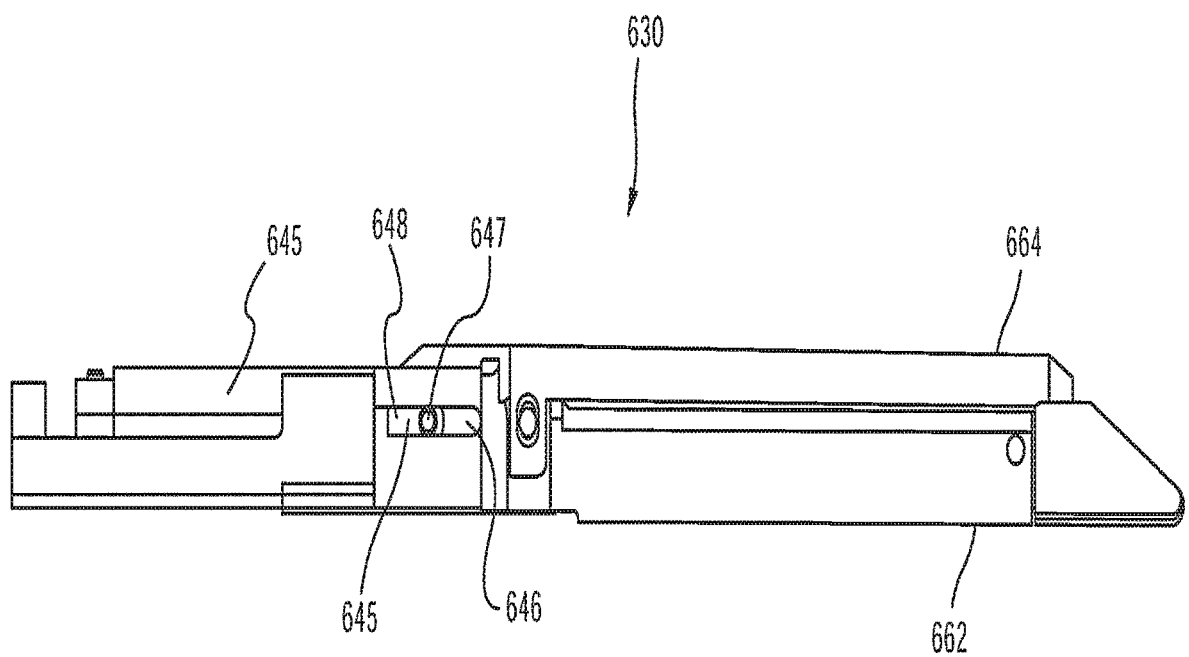
FIG. 6A illustrates a side view of a tissue interaction portion and a portion of an extension portion having an outer sheath removed, of a medical device, according to one embodiment of the invention.
Figure 6B:
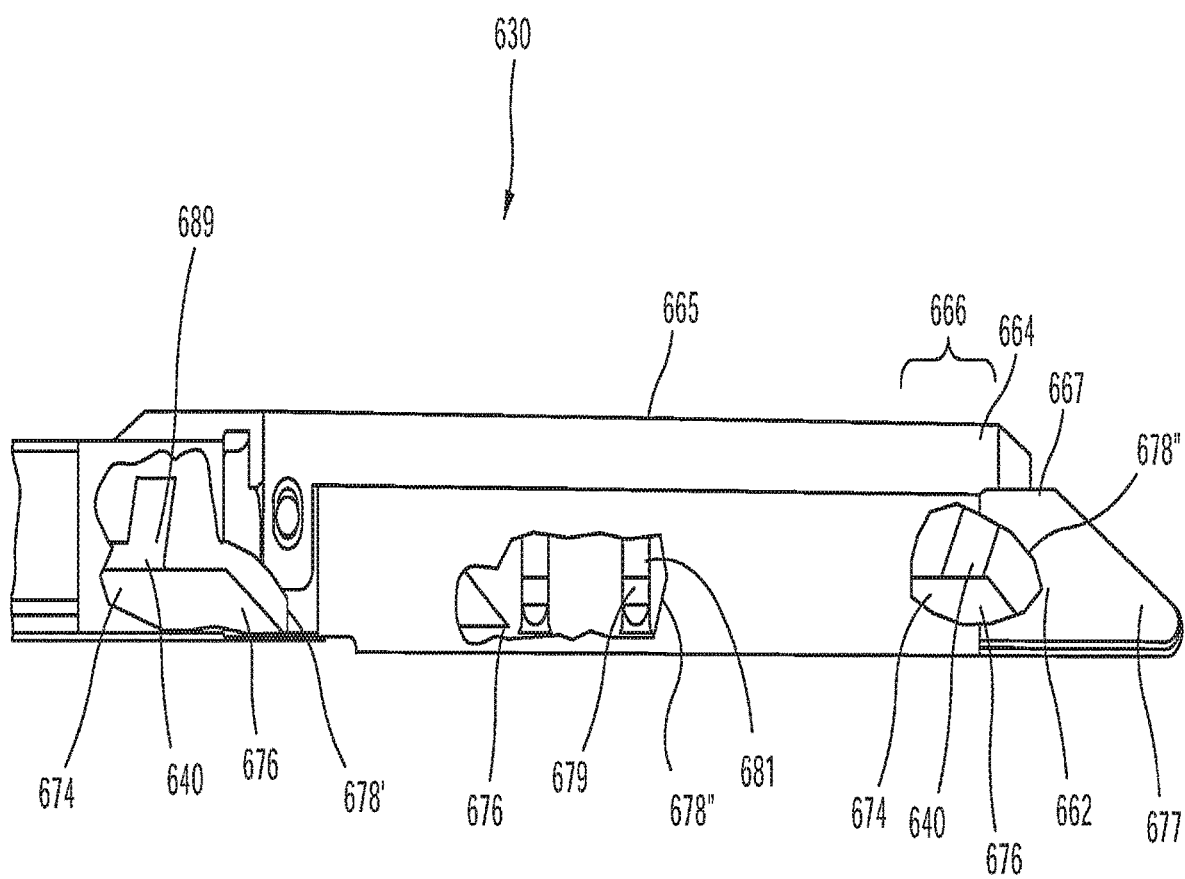
FIG. 6B illustrates a side view of a tissue interaction portion having a plurality of cut-outs according to one embodiment of the invention.
Figure 7:
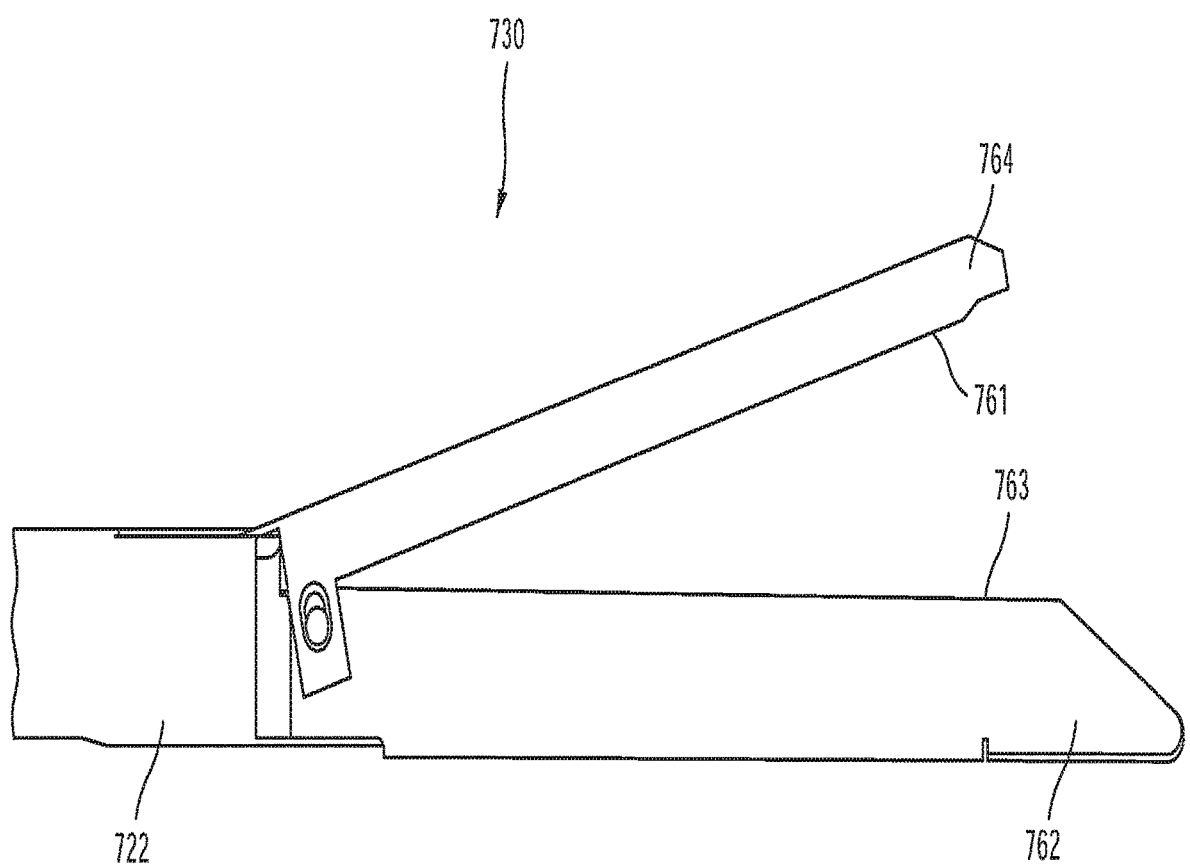
FIG. 7 illustrates a side view of a tissue interaction portion in a having an open clamping section according to one embodiment of the invention.

Turning now to FIGS. 6A, 6B and 7, seen is the tissue interaction portion 630, 730 of the medical device 100 seen in FIG. 1. The tissue interaction portion 630 comprises a base section 662 and a clamping section 664. The clamping section 664 individually or together with the base section 662 may also be referred to as a gripping mechanism. Other gripping mechanisms not using a clamping section 664 and a base section 662 are contemplated. For example, two pivotable clamping sections 664 may be used. The view in FIG. 6B is of an "overclamped" closed clamping section 664. Such an overclamped closed clamping section 664 may comprise a bend 665 in the closed clamping section 664 due to a distal portion 666 of the clamping section 664 pressing against an upper surface 667 of the base section 662 upon rotating down from the open position seen in FIG. 7 to the closed position seen in FIG. 6B.

Seen in FIG. 7 the view is of an open clamping section 764. Switching between the open clamping section 764 and closed clamping section 664, and vice versa, may be obtained by performing one or more actions at the actuator 110, as seen in FIG. 1. For example a user of the device 100 may either pull or push at least one of a first actuator trigger 112' and one or more second actuator triggers 112". Seen in FIG. 6A is a view of the tissue interaction portion 630 as the clamping section 664 initially touches the base section 662. Through the use of the actuator 110 and a biasing device (not shown) such as, but not limited to, a spring, a clamping/telescoping connector 645 may interact with the clamping section 664 to open and close the clamping section 664. The position of the clamping/telescoping connector 645 seen in FIG. 6A is the mid-way point between the open position seen in FIG. 7 and the closed position of FIG. 6B.

In one embodiment, the open clamping section 764 seen in FIG. 7 may be used as a clamping section starting point in selecting a desired tissue to interact with. For example, the desired tissue may be placed between the open clamping section 764 and the base section 762. Upon actuating the trigger 112, as seen in FIG. 1, the clamping section 764 may close, with a bottom clamping section surface 761 being located proximal a base section top surface 763, and the tissue being placed between the clamping section 764 and the top surface 763. It is contemplated that throughout the specification, where appropriate, the term "tissue" may comprise any internal or external part of a human, or even in an animal in a veterinary design. In one embodiment, the term "tissue" may refer to connective, muscle, nervous or epithelial tissue. It may also refer to organs or bones, or any other item contemplated but not listed or described above.

Figure 8:
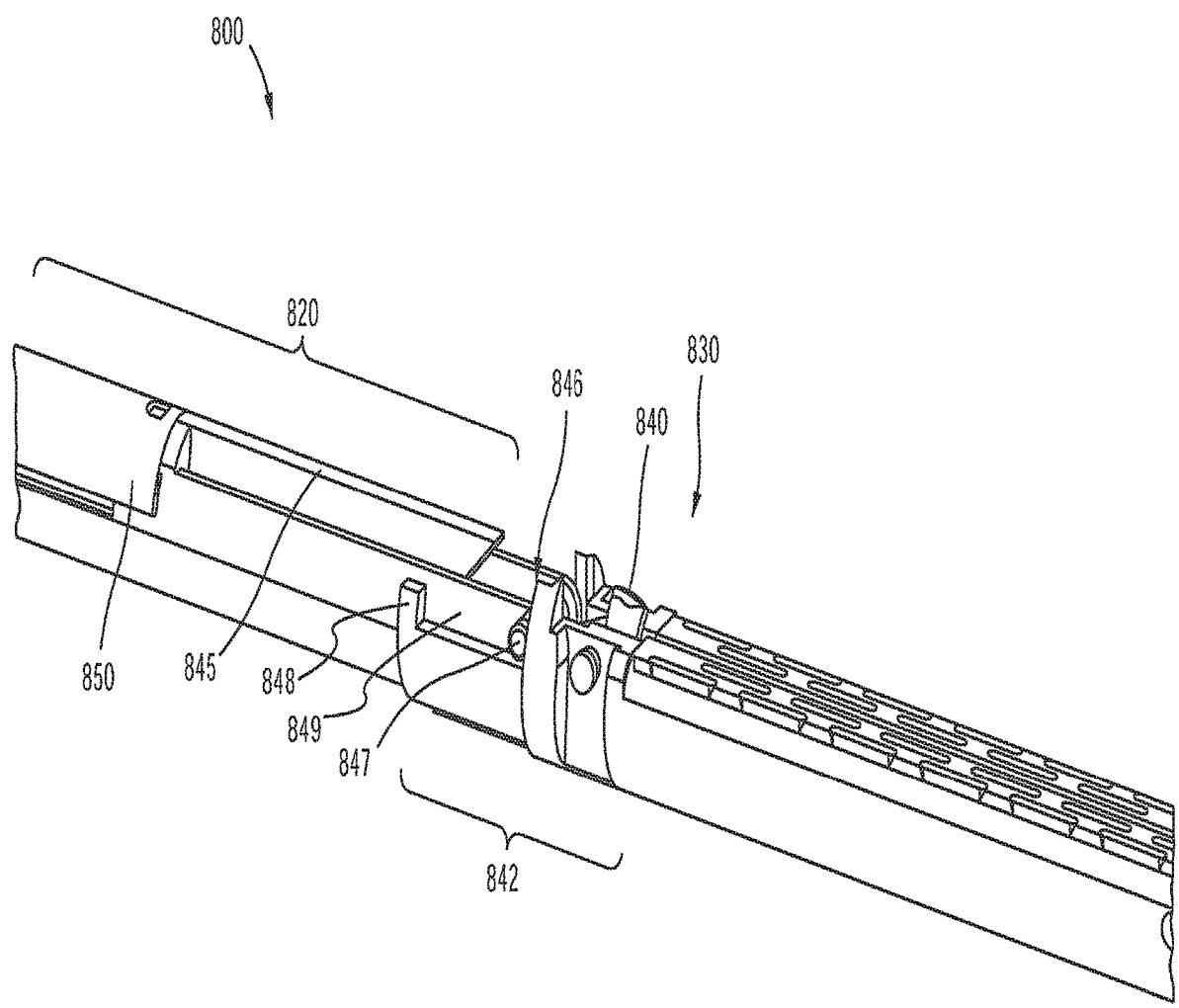
FIG. 8 illustrates an isometric view of a portion of a tissue interaction portion having at least a clamping section removed, and an extension portion in a retracted location with an outer sheath being removed according to one embodiment of the invention.

Turning now to FIG. 8, seen is one embodiment of the tissue interaction portion 830 and extension portion 820 in the open position seen in FIG. 7. In FIG. 8, the outer sheath 722 and clamping section 764 from FIG. 7 have been removed. Other portions of the medical device 800 may also have been removed in order to facilitate proper viewing of internal aspects of the device 800 in FIG. 8. Similarly, in other figures, one or more portions of the device 100 may be removed to facilitate proper viewing of the device 100 or device section. Returning now to FIGS. 8, 9 and 2, a medical device 800 may further comprise a cutting mechanism 840-240-940. The cutting mechanism 840 may comprise one or more metal or composite medical cutting blades. As seen in FIGS. 7 and 8, when the clamping section 764 is in an open mode, the cutting mechanism 840 may be located in a distal section 842 of the tissue interaction portion 830.

Figure 9:
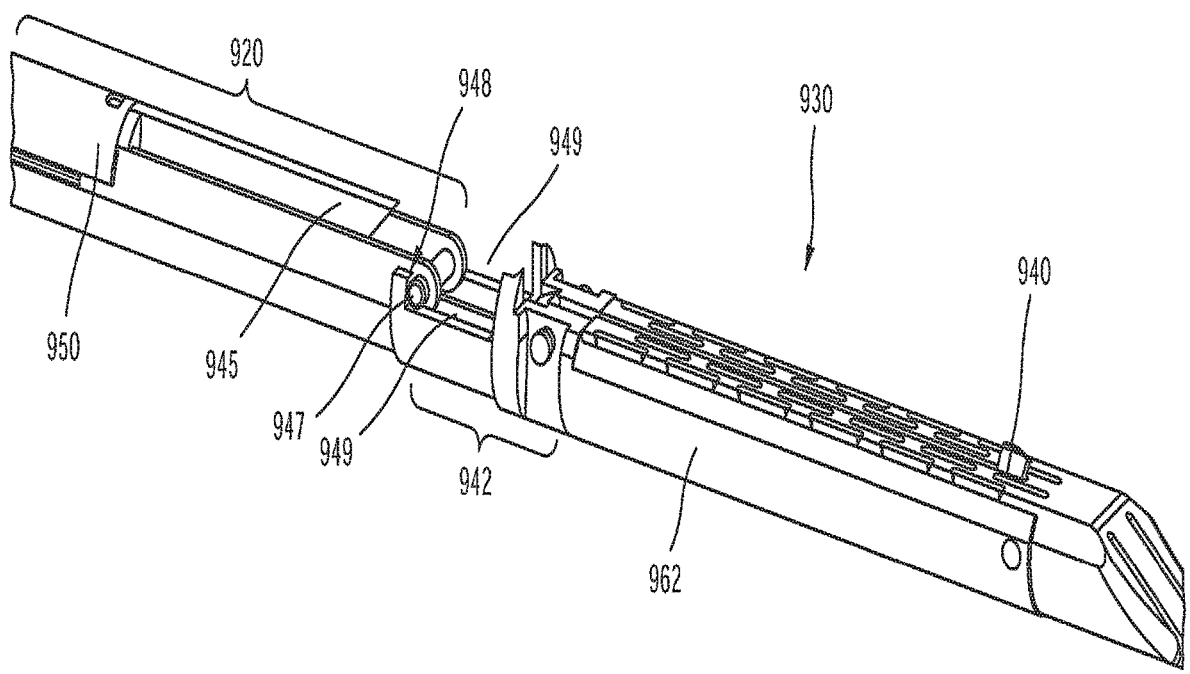
FIG. 9 illustrates an isometric view of a tissue interaction portion and a section of an extension portion in an extended location with an outer sheath and clamping section being removed according to one embodiment of the invention.

The tissue interaction portion 830 comprises the clamping/telescoping connector 845. In the open position, which may also be referred to as an open mode, seen in FIG. 8, the clamping/telescoping connector 845 may be located in a first position. In the first position, a distal end 847 of the clamping/telescoping connector 845 is located proximate to a base section notch leading edge 846. As seen in FIGS. 6A, 8 and 9, upon closing the clamping section 664, the distal end 647-847-947 of the clamping/telescoping connector 945 may travel from the leading edge 646-846-946 to a base section notch trailing edge 648-848-948. The leading edge 646-846-946 and trailing edge 648-848-948 may be opposing ends of at least one base section notch 849-949, as seen in FIGS. 8 and 9.

Seen in FIG. 9 is a pair of base section notches 949 located on opposing outer edges of the distal portion 942 of the base section 962. Greater or lesser notches 949 are contemplated. One of the notches 949 may be adapted to receive the clamping/telescoping connector 945. Other designs of the tissue interaction portion 930 adapted to interact with the telescoping portion 920 and/or the clamping/telescoping connector 945 besides the notch 949 are contemplated. For example, in one embodiment the clamping/telescoping connector 945 may be adapted to interact with the telescoping sections 224 seen in FIG. 2 and/or the clamping section 764 seen in FIG. 7. In one embodiment, as the telescoping sections 224 switch from the extended setting 432 of FIG. 4 to the retracted setting 534 of FIG. 5, the clamping/telescoping connector 945 interacts with the clamping section 664 to close the clamping section 664.

Returning again to FIG. 9, one portion of the clamping/telescoping connector 945 may slide along the notch 949 from the leading edge 946 to the trailing edge 948 upon closing the clamping section 664. Such movement of the clamping/telescoping connector 945 may also lead to interaction of the clamping/telescoping connector 945 with the clamping sheath 950. For example, upon changing the clamping section 764 from the open position seen in FIG. 7 to the closed position seen in FIGS. 6A and 6B, the clamping sheath 850 may be pushed from a first location/position, as seen in FIG. 8, to a second location/position, as seen in FIG. 9. FIG. 10A also shows the clamping sheath 1050 and clamping/telescoping connector 1045 located in a first location and first position, while FIG. 10B shows the clamping sheath 1050 and clamping/telescoping connector 1045 in a second location and second position. Moving from the first location to the second location may position a first clamping sheath notch 1051 to interact with a locking sheath tab 1052 after staples have been fired in the tissue interaction portion 1030, as seen in FIG. 10A′, which is a close up of box 10A′ from FIG. 10A. For example, after the staples have been fired, the locking sheath 1060 may retract to the position seen in FIG. 10A′. If the locking sheath 1060 attempts to move towards the tissue interaction portion 1030, moving to and past the position seen in FIG. 10B′, the locking sheath tab 1052 interacts with a notch 1051 wall, preventing the locking sheath 1060 and coupled staple rod 1154, as seen in FIG. 11, from moving.

Also seen in FIG. 10A are boxes 11 and 10A′. A close-up view of box 11 with the clamping sheath 1050 may be seen in FIG. 11B. FIG. 11A is the same view as seen in FIG. 11B, but without the clamping sheath 1150. Each of FIGS. 11A and 11B comprise the clamping position seen in FIG. 10B and are aligned in a manner similar to FIG. 1, with the actuator 110 being located to the left of FIGS. 11A and 11B and the tissue interaction portion 130 being located to the right of FIGS. 11A and 11B, as FIGS. 11A and 11B are displayed and aligned. Similar alignment of the device 100 may be associated with the other figures, unless otherwise stated.

As seen in FIG. 11B, in addition to the first locking sheath tab 1152-1052 discussed in reference to FIGS. 10A to 10B′ above, the clamping sheath 1150 may also comprise a second locking sheath tab 1153 and a third locking sheath tab 1198. The second locking sheath tab 1153 and third locking sheath tab 1198 may interact with the staple rod 1154. For example, as seen in FIG. 11B, a forward edge 1171 of the third locking sheath tab 1198 may contact a leading surface 1172 of a raised staple rod surface 1173. In one such embodiment, the staple rod 1154 moves towards the tissue interaction portion 130 seen in FIG. 1 when use of (i) a coupling mechanism such as, but not limited to a stapling mechanism, and/or (ii) a cutting mechanism such as, but not limited to, a blade, is desired at the tissue interaction portion 130 and a trigger 112 is activated at the actuator 110, as seen in FIG. 1. In one such case, the leading surface 1172 contacts the forward edge 1171, moving the clamping sheath 1150 along with the staple rod 1154 towards the tissue interaction portion 130. It is contemplated, although the terms "edge," "surface" or similar terms are used throughout the specification and/or claims, such terms are not intended to limit the disclosure to any specific design or feature type.

Turning now to FIG. 12, seen is one example of a start position of the locking sheath 1260 and staple rod 1254 upon initiating the coupling mechanism and/or cutting mechanism. One coupling mechanism may comprise a stapling device. In one such embodiment, as the staple rod 1254 moves toward the tissue interaction device 130, the leading surface 1256-1356 interacts with and pushes the locking sheath 1260 forward from the FIG. 12 position to the position seen in FIG. 13. The position of the staple rod 1354 seen in FIG. 13 is the position where the staple rod 1354 begins to interact with the at least one cutting mechanism 1340. In one embodiment, the at least one cutting mechanism 1340 may comprise a sharpened blade, with FIG. 13 showing a distal end 1388 of the blade and a first cutout 678′ of FIG. 6 showing a proximal end 689 of the blade, with the proximal end comprising a blade edge. Therefore, in one embodiment, the cutting mechanism 640-1340 extends from the staple rod 1354 to the tissue interaction portion 130. In one such embodiment, the cutting mechanism 640-1340 may also extend through extend through a middle notch 339′ of the telescoping section 324 seen in FIG. 3, while staple pushers 1574-274, as seen in FIGS. 15 and 2, may extend through the outer notches 339.

Returning now to FIG. 13, as seen, upon contacting the cutting mechanism 1340, the staple rod 1354 is adapted to continue to push the cutting mechanism 1340. As seen in FIG. 6, the cutting mechanism 640 may be moved from the position seen in the first cutout 687′ of FIG. 6 to the position seen in the third cutout 678′″ of FIG. 6. During the movement of the staple rod 1354, as seen in FIG. 13, two or more staple pushers 674, as seen in FIG. 6, may also be transitioned along a substantially similar movement.

For example, turning now to FIG. 15, seen is one embodiment comprising two staple pushers 1574 coupled to the staple rod 1554. FIG. 15 may be a starting position of the staple pushers 1574 and cutting mechanism 1540 prior to movement of the staple rod 1554. In one such embodiment, the staple pushers 1574 may comprise a raised leading section 1591 and a raised following section 1592 so that as the staple rod 1554 extends towards the tissue interaction portion 630 seen in FIG. 6 (and subsequently retracting), the staple pushers 1554 will substantially move with the movement of the staple rod 1554. However, since the cutting mechanism 1540 only comprises the raised following section 1592, the cutting mechanism 1540 will only begin to move upon contacting the raised leading surface 1156-1256-1556, as seen in FIGS. 11A, 12 and 15. The movement of the cutting mechanism 1540 is delayed in one embodiment relative to the staple pushers 1574. Therefore, the staple pushers 1574 may begin movement at a first time and the cutting mechanism 1540 may move at a second time, or vice versa. In one embodiment, the staple rod 1554 may also be referred to herein as a "rod" or a "at least one rod," and similar references. Similarly, at least a portion of the staple pushers 1574 may be referred to herein as a stapling shaft and at least a portion of the cutting mechanism 1540 may be referred to as a "cutting shaft."

Being pushed by the staple rod 1354, and continuing to move towards the tissue interaction device 630, an opposing end of the at least one cutting mechanism 1340, which may comprise a wedge 676, as seen in a first cutout 678′ of FIG. 6, may move from the first wedge position seen in the first cutout 678′ through the second wedge position seen in the second cutout 678″, and to the third wedge position seen in the third cutout 678′″. In one embodiment, the third wedge position is proximate a base section distal end 677. It is also contemplated that the wedge 676 and the cutting mechanism 640 may be adapted to extend towards the base section distal end 677 though one or more grooves or bores that may extend longitudinally through the base section 662. Such grooves or bores may be seen in FIGS. 8 and 9. Within one of the one or more grooves or bores which the wedge 676 is adapted to extend through may be a staple 681 resting on a staple base 679, as shown in the second cutout 678″. The wedge 676 may contact the staple base 679, forcing the staple base 679 and attached staple 681 upward toward the clamping section 664. Upon reaching the tissue clamped between the clamping section 664 and the base section 662, the staple may pierce the tissue and secure the tissue upon contacting an undercarriage of the clamping section 664. Seen in FIG. 14 is one example of a clamping section 1464 and a clamping section undercarriage 1478. The cutting mechanism 40 seen in FIG. 13 may subsequently cut the tissue and traveling through a clamping section notch 1479 in the process. To limit flexure during this process, without a large instrument cross section, the clamping section 1464 may include ridged sections 1466 along one or more of the edges of the clamping section 1464. The ridged sections 1466 may in some embodiments interlock with one or more clamping recesses 968 of the base section 962, shown in FIG. 9. This configuration further prevents transverse deflection from a longitudinal axis of the clamping section 1464, and otherwise improves alignment between the clamping section 1464 and the base section 962.

The cutting mechanism 640 may also extend through one of the notches 339 seen in FIG. 3. For example, the cutting mechanism 640 may extend through a middle notch 339'. FIG. 6B shows one portion of the cutting mechanism 640 through the first cutout 678'. The cutting mechanism 640 may travel from the first cutting mechanism position seen in the first cutout 678' to the second cutting mechanism position seen in the third cutout 678", cutting the tissue, and traveling through a clamping section notch 1479 in the process.

In one embodiment, the wedges 676 of the one or more staple pushers 674 may travel through the tissue interaction portion 130 seen in FIG. 1 before the cutting mechanism 640. This may be accomplished by initiating movement of the cutting mechanism 640 towards the tissue interaction portion 630 after movement of the one or more staple pushers 674 is initiated towards the tissue interaction portion 630. For example, the staple rod 1554 may first move from a first staple rod position seen in FIG. 15 to a second staple rod position seen in FIG. 13 before the cutting mechanism 1540-1340 begins to move. During this movement of the staple rod 1554 from the first position of FIG. 15 the wedge 676 may move from the first position seen in the first cutout 678' to the third position seen in the third cutout 678''', operatively contacting the staples 681 in the process. The movement of the cutting mechanism 640 from the first position seen in the first cutout 678' to the second position seen in the second cutout 678" may be delayed relative to the movement of the wedge 676 from the first position seen in the first cutout 678' to the second position seen in the third cutout 678". Therefore, the tissue clamped between the clamping section 664 and the base section 662 may be stapled before it is cut. The clamping section 1464 is also seen in FIG. 14.

When the cutting mechanism 640 and the wedge 676 are extended to the position seen in the third cut out 678", the staple rod 1754 may be fully extended towards the tissue interaction section 630. It is contemplated that throughout the specification and claims, though the term "extended" and "telescoping" are used to describe movement of various device features, the actual features of the device 100 may not be extendable or telescoping device features, the terms may simply refer to the device features moving to a different location. For example, as described above with reference to FIGS. 11A and 11B, and in further referring to FIGS. 1 and 17, as the staple rod 1754 extends towards the tissue interaction portion 130, the locking sheath 1760 may be coupled to the staple rod 1754 and may therefore travel with the staple rod 1754 towards the tissue interaction section 130. Upon retraction of the staple rod 1754, occurring after the staples 681 are coupled to the tissue and the cutting mechanism 640 is actuated, an action may occur at the actuator 110 in order to retract the staple pusher 1754. As seen in FIG. 17, a rear leading edge 1797 of the staple pusher 1754 may contact the second locking sheath tab 1753 and push the locking sheath 1760 upon the staple rod 1754 being retracted, retracting the locking sheath 1760 along with the staple pusher 1754. In retracting the locking sheath 1760, the first locking sheath tab 1152 of the locking sheath 1760 will eventually reach a first clamping sheath notch 1851-1051. As seen in FIGS. 18 and 10, the first clamping sheath notch 1851-1051 prevents the locking sheath 1060-1860 from returning towards the tissue interaction portion 130 as the tab 1052 would contact an edge of the notch 1051 if attempted to do so. Therefore, the locking sheath is kept in place upon retracting, and limiting the device 100 to a single use.

Therefore, a first action on the actuator 110 of FIG. 1 or another actuator known in the art, may move the tissue interaction portion 630-730 from the open position seen in FIG. 7 to the closed position seen in FIGS. 6A and 6B. Such first action, or a second action on the actuator 110 may also move the staple rod 1554 seen in FIG. 15 towards the tissue interaction portion 630, 730. Such movement of the staple rod 1554 also moves the clamping sheath 1560, staple pushers 1574, and cutting mechanism 1540 towards the tissue interaction portion 130. Upon release of the first or second action, or upon a third action at the actuator 110, the staple rod 1154 and clamping sheath 1150 move from the position seen in FIG. 11B to the position seen in FIG. 18, retracting the staple pushers 1574 and cutting mechanism 1540, preventing extension of the staple rod 1154 a second time. Such a mechanism may be referred to herein as a single application device. Additionally, it is contemplated that the movement of the rod 1554, sheath 1560, pushers 1574 and cutting mechanism 1540 described herein may be substantially parallel to the longitudinal axis 325 seen in FIG. 3.

Turning now to FIG. 16, seen is a method 1691 of using a medical device 100. One method 1691 starts at 1601 and at 1611 comprises performing a first function on the device actuator 110. It is contemplated that at least one first function may comprise use of the one or more triggers 112 seen in FIG. 1.

At step 1621 the method 1691 comprises moving the single-use mechanism described above from a first location to a second location. The single-use mechanism may also comprise the clamping sheath 1050. Moving the clamping sheath 1050 from the first location to the second location may comprise moving the clamping sheath 1050 from the first location seen in FIG. 10A to the second location seen in FIG. 10B.

At 1631 the method 1691 may comprise performing a second function on the device actuator 110. One second function may comprise a function similar to the first function such as, but not limited to, using one or more triggers 112. Upon performing the second function, and as seen at step 1641, the method 1691 may comprise moving a first section of a medical device extension portion 120 from a first retracted location to a second extended location. The medical device extension portion 220 may comprise the staple rod 254 and telescoping sections 224 seen in FIG. 2. Moving the staple rod 254 and telescoping sections 224 from a first retracted location to a second extended location may comprise moving the staple rod 1554 from an initial starting position (i.e., the first retracted location), as seen in FIG. 15, to a fully extended position (i.e., the second extended location), as seen in FIGS. 11A and 11B. The movement of the staple rod 1154-1554 from the first position to the second position may comprise moving the staple rod distal end 1193-1593 towards the tissue interaction portion 130, as seen in FIG. 1. It should be noted that FIGS. 11A, 11B, and 15 may have one or more portions of the device 100 seen in FIG. 1 removed in order to better view other portions of the device 100. Specifically, at least the telescoping sections 224 have been removed from FIGS. 11A, 11B and 15 in order to provide a clearer representation of the operation of the staple rod 1154-1554, cutting mechanism 1540-1140, staple pushers 1574, and clamping sheath 1150-1550. It is fully understood that as the staple pusher 254 moves towards the tissue interaction portion 230, as seen in FIG. 2, the staple pusher 254 will interact with the one or more telescoping sections 224 such that upon performing the second function, the one or more telescoping sections 224 move from the first retracted position, as seen in FIG. 4 to the second extended position seen in FIG. 5. Therefore, as shown in step 1651, the method 1691 further comprises extending a plurality of extension portion telescoping sections 224.

As the staple rod 254 moves towards the tissue interaction portion 230, and as seen in FIG. 15 and described above, the staple rod 254 may push against the raised leading section 1591 of the one or more staple pushers 1574, moving the one or more staple pushers 1574 towards and through the tissue interaction portion 230. As seen in FIG. 6B, upon the staple rod pushing the one or more staple pushers 674, a wedge 676 portion of the staple pusher 674 may move from the location seen in the first cutout 678' to the position seen in the third cutout 678", encountering the staple base 679 seen in the second cutout 678" in the process. The wedge 676 would then push the staple base 679 and coupled staple 681 towards the tissue located between the clamping section 664 and the base section 662. The staple 681 may then attach to the tissue. In one embodiment, the staple 681 and/or staple base 679 may comprise a coupling device, and at step 1661 the method comprises attaching the coupling device to the tissue.

Returning now to FIGS. 2 and 15, as the staple rod 254-1554 moves from the position seen in FIG. 15 toward the tissue interaction portion 230, the staple pusher 1254, as seen in FIG. 12 will approach the cutting mechanism 1240, and eventually interact with the cutting mechanism 1354, as seen in FIG. 13. At this point, as seen in step 1671 of the method 1691, and returning now to FIG. 6B, the cutting mechanism 640 is pushed towards the distal end 677 of the base section 662 of the tissue interaction portion 630, cutting the tissue as it travels to the location seen in the third cutout 678'''.

The method 1691 may further comprise moving a first section of a medical device extension portion 120, as seen in FIG. 1, from a first retracted location to a second extended location. The first section may comprise a rod, herein referred to as at least one staple rod 254, also referred to herein as at least one stapling shaft. Such a staple rod 254 may move from a first stapling shaft location such as, but not limited to the stapling shaft position seen in FIG. 15 and the location of the staple pusher 674 seen in the first cutout 678' to a second stapling shaft location, such as, but not limited to the location of the staple pusher 654 seen in the third cutout 678''' and the staple rod 1354 seen in FIG. 13.

In one embodiment, the step 1661 of attaching a coupling device to tissue may further comprise interacting at least one stapling shaft proximal end with at least one staple receiving device. For example the wedge 676 may comprise a proximal end and the base section 679 may comprise a staple receiving device.

The single-use mechanism may also be referred to as the clamping sheath 1050 and/or the locking sheath 1060, and the clamping sheath 1050 may be referred to as an inner clamping sheath. In the method 1691, a third function on the device actuator 110 seen in FIG. 1 may retract the staple rod 254 from the second extended location. The inner clamping sheath 1050 and the locking sheath 1060 may prevent the rod 254 from returning to the first retracted location by coupling the rod 254 to the locking sheath 1060 and the locking sheath 1060 to the clamping sheath 1050. The inner clamping sheath 1060 may prevent the rod 254 from returning to the first retracted location by coupling the rod 254 to the clamping sheath 1050 at a retracted location.

Extending at least one staple pusher 1574, also referred to herein as a stapling shaft, from a first stapling shaft location to a second stapling shaft location may comprise positioning the at least one stapling shaft in at least one notch 339 located in the plurality of extension portion telescoping sections 324, as seen in FIG. 3, and sliding at least a portion of the at least one stapling shaft through the at least one notch 339. Similarly, the cutting mechanism 640 may be referred to herein as at least one cutting shaft, which may be positioned in at least one notch 339 and at least a portion of the at least one cutting shaft may be slid through the at least one notch 339. The outer sheath 122 may prevent buckling of the extension portion telescoping sections.

The device 100 described above, or at least a portion thereof, may also be referred to herein as a tissue coupling system. For example, the tissue coupling system may also comprise the actuator 110 and the plurality of telescoping sections 432 operatively coupled to the actuator 110, as seen in FIGS. 1 and 4. Alternatively, the tissue coupling system may only comprise the extension portion 220 as seen, for example, in FIG. 2 and/or the tissue interaction portion 630 of FIG. 6, for example. Each of the telescoping sections 432 may comprise an upper section 401 and a lower section 403, as seen in FIG. 4. The upper section 401 may comprise at least one upper section slot 423, while the lower section 403 may comprise at least one lower surface slot 439. The tissue coupling device 130 seen in FIG. 1 and elsewhere may be coupled to at least one of the plurality of telescoping sections 432. Each of the at least one upper section slot 423 may be adapted to receive one of a portion of another telescoping section 432 and at least a portion of the tissue interaction portion 130. In one embodiment, at least one tissue interaction portion 130 may be referred to as a tissue coupling device.

The tissue coupling device may couple to one or more of a plurality of telescoping sections 432. One or more telescoping sections may be added to and/or removed from the tissue coupling system to one of shorten and lengthen the tissue coupling system. For example, one or more of the plurality of telescoping sections 432 may be one of added to and removed from the tissue coupling system to access a desired tissue.

In one embodiment, the tissue coupling system may further comprise a locking mechanism adapted to limit use of the tissue coupling device to user-specified number of actions. For example, the locking mechanism may comprise the locking sheath 1050, coupling sheath 1060, and/or the staple rod 1154. At least one of the sheaths may comprise at least one, or a plurality of tabs, as shown and discussed above with respect to FIG. 11. Each of the plurality of tabs may be adapted to interact with another sheath and/or a rod such as, but not limited to, the staple rod 1154. At least one of the tabs may interact with a notch of another sheath.

The embodiment may be adapted to release the locking mechanism at the actuator and re-fire the additional staples. In other embodiments where the tissue coupling device comprises a tissue stapler, a user-specified number of actions may comprise a single-use before resetting occurs-such as, but not limited to, inserting additional staples 681 into the device.

Referencing now FIGS. 19-24B, other embodiments are now discussed. In some of these embodiments, it is contemplated that a device is provided, wherein the device has one or more telescoping sections 2024"-2024', a spacer section 2044, and an elongated spacer section 2084, each of which is movable in relation to one another and a device sheath from a pre-action configuration, to an action configuration, to a return configuration. For the purpose of describing these embodiments, it should be understood that the term "pre-action" is intended to describe the state of the device prior to surgical manipulation of tissue, such as prior to firing staples, moving a knife, or causing a tissue interaction device to grip tissue. Causing the device components to move relative to one another to directly or indirectly manipulate tissue is an "action", such as, but not limited to, firing or causing staples to fire, gripping or causing a gripping device to grip tissue, or cutting or causing a cutting device to cut tissue.

Turning now to FIG. 19, seen is an isometric exploded view of an actuator 1910 according to another embodiment. As seen, a resistance element 1914 may be provided between an actuator knob 1915 of the actuator 1910 and the handle of the actuator 1910. The resistance element 1914 may be a friction nub made of a semi-flexible material such as silicone, rubber, or other polymeric materials, with it being understood by those skilled in the art that other materials may be used, and a desired resistance between the actuator knob 1915 and the handle can be controlled by the resistance element 1914. That is, the resistance element 1914 dampens the rotation of the actuator knob 1915 against the handle, or causes the knob to resist rotation, preferably creating enough resistance that substantially consistent force is required to cause the actuator knob 1915 to rotate over the entire 360 degrees of rotation. The resistance element 1914 may also maintain the instrument shaft clocking during tissue manipulation. In other words, the resistance element 1914 serves to maintain the instrument shaft in a steady position after the user has rotated the actuator knob 1915 to a desired location, remaining in the desired location until and unless another rotation is initiated by the user.

The resistance element 1914 may provide further advantages in the course of manufacturing. For example, in embodiments having a molded or semi-flexible actuator knob 1915, the resistance element 1914 may compensate for some of the deviation from a desired roundness, thus loosening some of the otherwise tight manufacturing tolerance requirements that may be required of the actuator knob 1915.

Turning now to FIG. 20, shown is a side view of another embodiment of the device. This embodiment comprises an extension portion 2020 having two telescoping sections 2024'-2024", a spacer section 2044 proximal to the telescoping sections 2024'-2024", and an elongated spacer section 2084 proximal to the spacer section 2044. The distal end of the extension portion 2020 comprises a clamping/telescoping connector 2045 similar to the clamping/telescoping connector 845 previously described with reference to FIGS. 1-18 and is further coupled to a tissue interaction portion 2030. An insert 2094 is also shown in FIG. 20, which will be described in further detail below, with reference to FIGS. 24A-24B.

In the embodiment shown in FIG. 20, the telescoping sections 2024'-2024" are configured like the telescoping spacers 224-324-424-524 discussed with reference to FIGS. 1-18. The telescoping sections 2024'-2024", the spacer section 2044, and the elongated spacer section 2084 are configured to move within a sheath, which is not shown, and relative to each other in a manner similar to the telescoping sections 224 described with reference to FIGS. 1-18, with differences to be discussed below. The telescoping sections 2024'-2024" provide support to a portion of the surgical action mechanism 2074, which may be a staple pusher, and the spacer section 2044 provides support to another portion of the surgical action mechanism 2074. That is, the telescoping sections 2024'-2024", spacer section 2044, and elongated spacer section 2084 collectively may operate to stabilize the surgical action mechanism 2074, which may be one or more staple pushers, while in a pre-action configuration and an action configuration. It will be understood that, after the surgical action is complete, and the device is manipulated to a return configuration, such stability is not required, and the elongated spacer section 2084 no longer provides stability to the surgical action mechanism 2074.

To provide for a small incision size, which is particularly desirable in the course of pediatric surgery, each of the elongated spacer section 2084, the spacer section 2044, and the telescoping sections 2024'-2024" are preferably configured to fit within a diameter D that is less than about 5 millimeters. That is, the inner diameter of the clamping sheath 850 is preferably about 5 millimeters. In some embodiments, the inner diameter of the clamping sheath 850 is less than 5 millimeters.

The spacer section 2044 and the elongated spacer section 2084 may also be referenced as a first spacer and a second spacer respectively. Further, although the spacer section 2044 and the elongated spacer section 2084 are shown as having a particular relationship in size, i.e. the elongated spacer section 2084 is longer than the spacer section 2044, it should be understood by those skilled in the art that a different size relationship or configuration is possible. For example, the elongated spacer section 2084 could be shorter than the spacer section 2044.

As discussed, some embodiments provide for at least one surgical action mechanism 2074, which may be one or more staple pushers. In other embodiments, the surgical action mechanism 2074 may be a cutting device or a gripping device. In still other embodiments, the surgical action mechanism 2074 may be any combination of one or multiple staple pushers, a cutting device, and a gripping mechanism. It should be understood that some embodiments of the surgical action mechanism 2074 may be configured for direct interaction with tissue, such as a knife or cutting mechanism, while other surgical action mechanisms 2074 are configured to indirectly effect tissue manipulation. For example, staple pushers need not necessarily directly interface with tissue, yet they are nonetheless surgical action mechanisms 2074 for the purpose of this disclosure by virtue of their intended purpose of causing staples to engage tissue, or firing staples. Similarly, a gripping mechanism may be a sheath or rod that, upon actuation, causes the tissue interaction portion to close upon tissue, even where the gripping mechanism does not directly interact with tissue. It should also be understood that operation of the surgical action mechanism 2074 is in response to a manipulation of a device actuator.

With reference now to FIG. 21, the spacer section 2144 is now discussed in more detail. The spacer section 2144 is configured to disengage from, or fail to follow, the elongated spacer section 2084 after a surgical action is performed. Spacer section 2144 comprises a body section 2148 that is adapted to receive an attachment section 326 of a telescoping section 324, and is generally configured in a manner similar to the telescoping section 324 shown in FIG. 3. Unlike the telescoping section 324, however, spacer section 2144 does not comprise an attachment section. Without an attachment section, the spacer section 2144 becomes disengaged from the elongated spacer section 2084 after an action is performed, thereby preventing telescoping sections 224'-224" from being pulled back to their pre-action positions, thus reduction the forces over which the actuating and return mechanism must overcome reach a return configuration. It is contemplated that multiple telescoping sections 2024'-2024" are used with a single spacer section 2044, as is shown in FIG. 20; however, a single telescoping section 2024' may be used in some embodiments.

Turning now to FIG. 22, shown is a side view of the elongated spacer section 2284 shown in FIG. 20. As seen, the elongated spacer section 2284 comprises a distal end 2213 that is configured in much the same manner as spacer section 2144 and telescoping section 324, and a proximal end 2217 that is configured to operatively engage an actuator assembly. In operation, and as seen with reference to FIGS. 20-23B, the elongated spacer section 2284 is configured to move within a sheath of the extension portion 2020 of the device, to cause the spacer section 2044, telescoping sections 2024'-2024", and the surgical action mechanisms 2374 or staple pushers to move to a surgical action position.

FIGS. 23A and 23B illustrate top views of the elongated spacer section 2384, spacer section 2344, and surgical action mechanisms 2374 in a pre-action or pre-firing configuration and a return or post-firing configuration respectively. As seen, at least one of the surgical action mechanisms 2374 comprises a bend or bias at the proximal/trailing end, the bias causing the surgical action mechanism 2374 to disengage from the elongated spacer section 2384 after firing, thereby causing the device to be limited to a single use, with it being understood that the term "single use" means a single surgical deployment, which may include a combination of multiple effects on tissue, such as cutting, coupling with one or more staples, and gripping. In some embodiments, this bend may be toward a side of the surgical action mechanism 2374, so that the trailing end of the surgical action mechanism 2374 may deviate approximately 1.5 mm, or about 0.5 inches, from a centerline defined by the surgical action mechanism 2374.

The bend 2319 in the trailing end of the surgical action mechanism 2374 may serve two purposes. First, as seen in FIG. 23A, the bend 2319 causes the trailing end of the surgical action mechanism 2374 to press against an interior of the elongated spacer section 2384 while the elongated spacer section 2384 confines the proximal end of the surgical action mechanism 2374 while the device is in the pre-action configuration. This confinement serves to provide friction between the surgical action mechanism 2374 and the elongated spacer section 2384 during shipping and other handling prior to use and firing. Such friction prevents the surgical action mechanism 2374 from inadvertently becoming displaced during shipment, thus improving reliability and predictability of the device. The present disclosure contemplates embodiments of the device being a surgical stapler capable of classic staple formation with B-shape staples, and, for the purpose of this disclosure, the term "staple pusher" should be understood as being one type of surgical action mechanism 2374, and used interchangeably for illustrative purposes.

Second, and as seen in FIG. 23B, the bend 2319 prevents the staple pusher 2374 from being re-fired after a single use, because, after firing, the bend 2319 in the trailing end of the staple pushers 2374 prevents the staple pusher 2374 from re-aligning with a recess in the elongated spacer section 2384.

Returning once again to FIG. 20, as seen, the spacer 2044 serves to disengage movement of the telescoping section 2024" from the movement of the elongated spacer section 2084. That is, upon firing, the elongated spacer section 2084 moves against the spacer section 2084, causing the spacer section 2084 and the telescoping sections 2024'-2024" to move from a pre-firing setting to a firing setting, the firing setting being a contracted setting similar to the settings discussed with reference to FIGS. 1-18 above. However, because of the disengagement, when the elongated spacer section 2084 is moved to a post-fire or return position, the spacer section 2044 and telescoping sections 2024'-2024" are not returned, instead remaining in a contracted state. Causing the disengagement in this manner reduces the return force experienced by an actuating mechanism, which may include a spring return, when moving from an action or firing position to a return or post-firing position, thus increasing the overall reliability of the device. Moreover, the disengagement between the spacer section 2044 and the elongated spacer section 2084 allows the staple pushers 2374 to disengage from the elongated spacer section 2384, as shown in FIGS. 23A-23B.

Turning now to FIGS. 24A and 24B, a side view and a partial section view of a lock feature in a return configuration are respectively shown. In FIG. 24A, a cartridge housing insert 2494 is shown encircling the clamping/telescoping connector 2445 and the staple pushers 2474 at a region near the wedge portion 2476 of the staple pushers 2474. For the sake of clarity, it should be understood that, in this view, certain other components, including the clamping sheath 850, outer sheath 722, and clamping section 764, have been removed. The cartridge housing insert 2494 may be a semi-flexible composite or plastic material configured to flex away from the center of the device when force is applied from within.

Moreover, and as shown in FIG. 24B, the cartridge housing insert 2494 may flex towards a neutral position post-fire, causing a lock feature 2496 on the interior of the cartridge housing insert 2496 to engage a catch feature 2495 in the staple pusher 2474.

Configuration of the catch feature 2495 in this manner prevents the staple pushers 2474 from returning to a pre-fire position after a single use. Moreover, the catch feature 2495 removes the need for the locking sheath tabs 1152-1153-1198 described above in reference to FIG. 11B.

Turning now to FIG. 25, a method 2500 is disclosed. As a part of the method 2500, a device is provided 2501, wherein the device is configured as described above. Further, the device is displaced 2511 between a first position and a second position while simultaneously preventing longitudinal displacement of the at least one surgical action mechanism.

The method 2500 may include actuating the device 2521 to simultaneously cause the first spacer, the second spacer, the at least one telescoping section, and the at least one surgical action mechanism to move relative to the at least one sheath from a pre-action configuration to an action configuration.

After actuating 2521, the method 2500 may include entering a return configuration 2531 by causing the first spacer, the second spacer, the at least one telescoping section, and the at least one surgical action mechanism to form a return configuration, by causing the second spacer and the at least one surgical action mechanism to move relative to the at least one sheath while simultaneously causing the first spacer and the at least one telescoping section to remain stationary relative to the at least one sheath.

The method 2500 may also include, after actuating, causing the at least one surgical action mechanism to disengage from the second spacer. In other embodiments, the method 2500 may include locking the at least one surgical action mechanism in a lock position, the lock position associated with the return configuration. The method 2500 may also include causing the proximal end of the at least one surgical action mechanism to exert a transverse force on the second spacer while the device is in the pre-action configuration.

In conclusion, some embodiments of the present invention provide for a device or system for use in laparoscopic surgery. Other embodiments provide for a method associated with the device. Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions fall within the scope and spirit of the disclosed invention as expressed in the claims.

What is claimed is:

1. A component of a surgical stapler, comprising:
    a first telescopic section having a body section and an attachment section coupled to the body section;
    a first spacer section configured to slidably receive the attachment of the first telescopic section; and
    a second spacer section,
    wherein the first spacer section is located between the body section of the first telescopic section and the second spacer section, and
    wherein the first spacer section is configured to engage with the second spacer section during a surgical action performed by the surgical stapler, and to disengage from the second spacer section after the surgical action is performed.

2. The component of the surgical stapler of claim 1, wherein the first telescopic section is distal to the first spacer section and the second spacer section.

3. The component of the surgical stapler of claim 1, wherein a distal end of the second spacer section is configured to mate with a proximal end of the first spacer section.

4. The component of the surgical stapler of claim 1, wherein the first spacer section is slidable relative to the second spacer section, and the first telescopic section is slidable relative to the first spacer section.

5. The component of the surgical stapler of claim 1, wherein the first telescopic section, the first spacer section, and the second spacer section collectively form a pre-action configuration before the surgical stapler is actuated, form an action configuration while the surgical stapler is actuated, and form a return configuration after the surgical stapler is actuated.

6. The component of the surgical stapler of claim 1, wherein a disengagement between the first spacer section and the second spacer section after the surgical action is performed reduces a force over which a mechanism of the surgical stapler is required to overcome to reach a return configuration.

7. The component of the surgical stapler of claim 1, further comprising a second telescopic section, wherein the first telescopic section is between the first spacer section and the second telescopic section.

8. The component of the surgical stapler of claim 7, wherein the body section of the first telescopic section is configured to receive an attachment section of the second telescopic section.

9. The component of the surgical stapler of claim 1, wherein the first spacer section comprises a channel configured to slidably accommodate a surgical action mechanism.

10. The component of the surgical stapler of claim 9, wherein the surgical action mechanism comprises a staple pusher.

11. The component of the surgical stapler of claim 9, wherein the surgical action mechanism comprises an elongated structure that is slidably accommodated in the channel of the first spacer section before the surgical action is performed, wherein a part of the elongated structure is configured to change shape after the part of the elongated structure exits from the channel due to the surgical action, and wherein the part of the elongated structure that has changed shape prevents the part of the elongated structure from being re-inserted into the channel after the surgical action is performed.

12. The component of the surgical stapler of claim 1, further comprising a sheath, wherein the first telescopic section, the first spacer section, and the second spacer section are at different respective longitudinal locations along a longitudinal axis of the sheath.

13. The component of the surgical stapler of claim 12, further comprising
    a tissue interaction portion; and
    a device actuator,
    wherein at least a part of the sheath is between the tissue interaction portion and the device actuator, and
    wherein the tissue interaction portion is configured to interact with tissue in response to a manipulation of the device actuator.

14. The component of the surgical stapler of claim 13, wherein the device actuator comprises a rod configured to move the first telescoping section and the first spacer section.

15. The component of the surgical stapler of claim 1, wherein the attachment section of the first telescopic section comprises a hook section having a neck portion and an extension section extending radially outward from a longitudinal axis of the attachment section.

16. The component of the surgical stapler of claim 1, wherein the first spacer section does not have any attachment section that directly attaches to the second spacer section after the surgical action is performed.

17. A component of a surgical stapler, comprising:
    a spacer section having a proximal end, a distal end, and a body extending between the proximal end and the distal end,
    wherein the body of the spacer section comprises an opening configured to receive an attachment section of a telescopic section of the surgical stapler, and
    wherein the proximal end of the spacer section is configured to engage with another spacer section during a surgical action performed by the surgical stapler, and to disengage from the other spacer section after the surgical action is performed.

18. The component of the surgical stapler of claim 17, wherein the body of the spacer section comprises a channel configured to slidably accommodate a surgical action mechanism.

19. The component of the surgical stapler of claim 18, wherein the surgical action mechanism comprises a staple pusher.

20. The component of the surgical stapler of claim 17, wherein the spacer section does not have any attachment section that directly attaches to the other spacer section after the surgical action is performed.

* * * * *